(12) United States Patent
Sall et al.

(10) Patent No.: US 7,087,635 B2
(45) Date of Patent: Aug. 8, 2006

(54) 3-SUBSTITUTED OXINDOLE β3 AGONISTS

(75) Inventors: Daniel Jon Sall, Greenwood, IN (US); Jolie Anne Bastian, Beech Grove, IN (US); Cynthia Darshini Jesudason, Indianapolis, IN (US); Don Richard Finley, Greenwood, IN (US); Freddie Craig Stevens, Indianapolis, IN (US); Vincent Patrick Rocco, Indianapolis, IN (US); Patrick Gianpietro Spinazze, Avon, IN (US); John Xiaoqiang He, Fishers, IN (US); John Arnold Werner, Indianapolis, IN (US); William George Trankle, Souhtport, IN (US); Andrew Michael Ratz, Indianapolis, IN (US); Theo Schotten, Vierhufen (DE); Gerd Reuhter, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 52 days.

(21) Appl. No.: 11/082,106

(22) Filed: Mar. 16, 2005

(65) Prior Publication Data

US 2005/0159473 A1    Jul. 21, 2005

Related U.S. Application Data

(62) Division of application No. 10/486,508, filed as application No. PCT/US02/21316 on Aug. 6, 2002, now Pat. No. 6,911,463.

(60) Provisional application No. 60/312,135, filed on Aug. 14, 2001.

(51) Int. Cl.
*A61K 31/40* (2006.01)
*A61K 31/38* (2006.01)
*C07D 209/54* (2006.01)
*C07D 317/08* (2006.01)
*C07D 409/00* (2006.01)

(52) U.S. Cl. ............ 514/409; 514/444; 514/469; 548/408; 549/59; 549/228; 549/229

(58) Field of Classification Search ............ 514/409
See application file for complete search history.

(56) References Cited

U.S. PATENT DOCUMENTS

| | | | |
|---|---|---|---|
| 4,276,304 A | 6/1981 | Ikezaki et al. | |
| 4,826,847 A | 5/1989 | Michel et al. | |
| 5,808,080 A | 9/1998 | Bell et al. | |
| 5,977,154 A | 11/1999 | Bell et al. | |
| 6,011,048 A | 1/2000 | Mathvink et al. | |
| 6,825,220 B1 * | 11/2004 | Jesudason et al. | 514/340 |

FOREIGN PATENT DOCUMENTS

| | | |
|---|---|---|
| DE | 2830884 | 1/1979 |
| EP | 166331 | 1/1986 |
| EP | 221414 | 5/1987 |
| EP | 236624 | 9/1987 |
| EP | 611003 | 8/1994 |
| EP | 678511 | 10/1995 |
| EP | 764640 | 3/1997 |
| EP | 827746 | 3/1998 |
| GB | 159945 | 8/1979 |
| WO | WO 95/29159 | 11/1995 |
| WO | WO 97/10825 | 3/1997 |
| WO | WO 97/46556 | 12/1997 |
| WO | WO 98/4526 | 2/1998 |
| WO | WO 98/9625 | 3/1998 |
| WO | WO 98/32753 | 7/1998 |
| WO | WO 00/40560 | 7/2000 |
| WO | WO 00/44721 | 8/2000 |
| WO | WO 01/7026 | 2/2001 |
| WO | WO 01/35947 | 5/2001 |
| WO | WO 01/36412 | 5/2001 |
| WO | WO 01/53298 | 7/2001 |
| WO | WO 02/6276 | 1/2002 |
| WO | WO 02/38543 | 5/2002 |

OTHER PUBLICATIONS

Lee, et al, *J. Het. Chem.*, 32(1):1-11, 1995.
Mathvink, *Bioorganic & Medicinal Chemistry Letters*, 9(13):1869-1874, 1999.
Shuker, A. J., et al. *Tetrahedron Letters*; 38(35):6149-6152, 1997.
Weber, et al., *Bioorganic & Medicinal Chemistry Letters*;8(9):1101-1106, 1998.
Weber, et al., *Bioorganic & Medicinal Chemistry Letters*;8(16):2111-2116, 1998.

* cited by examiner

*Primary Examiner*—Kamal A. Saeed
*Assistant Examiner*—Susannah L. Chung
(74) *Attorney, Agent, or Firm*—John C. Demeter; Gilbert T. Voy

(57) ABSTRACT

The present invention relates to a β3 adrenergic receptor agonist of formula I:

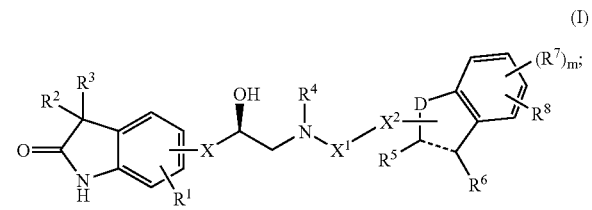

or a pharmaceutical salt thereof; which is capable of increasing lipolysis and energy expenditure in cells and, therefore, is useful for treating Type 2 diabetes and/or obesity.

4 Claims, No Drawings

3-SUBSTITUTED OXINDOLE β3 AGONISTS

This application is a division under 35 U.S.C. s121 of application Ser. No. 10/486,508 filed Feb. 11, 2004 now U.S. Pat. No. 6,911,463, which claims the benefit under 35 U.S.C. §120 of International Application No. PCT/US02/21316 filed Aug. 6, 2002, which claims the benefit under 35 U.S.C. § 119(e) of U.S. Ser. No. 60/312,135 filed Aug. 14, 2001.

The present invention is in the field of medicine, particularly in the treatment of Type 2 diabetes and obesity. More specifically, the present invention relates to $\beta_3$ adrenergic receptor agonists useful in the treatment of Type 2 diabetes and obesity.

The current preferred treatment for Type 2, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat either Type 2 diabetes or obesity.

One therapeutic opportunity that has recently been recognized involves the relationship between adrenergic receptor stimulation and anti-hyperglycemic effects. Compounds that act as $\beta_3$ receptor agonists have been shown to exhibit a marked effect on lipolysis, thermogenesis and serum glucose levels in animal models of Type 2 (non-insulin dependent) diabetes.

The $\beta_3$ receptor, which is found in several types of human tissue including human fat tissue, has roughly 50% homology to the $\beta_1$ and $\beta_2$ receptor subtypes yet is considerably less abundant. Stimulation of the $\beta_1$ and $\beta_2$ receptors can cause adverse effects such as tachycardia, arrhythmia, or tremors. An agonist that is selective for the $\beta_3$ receptor over the $\beta_1$ and $\beta_2$ receptors is, therefore, more desirable for treating Type 2 diabetes or obesity relative to a non-selective agonist.

However, recent studies have suggested the presence of an atypical $\beta$ receptor associated with atrial tachycardia in rats (*Br. J. of Pharmacol.*, 118:2085–2098, 1996). In other words, compounds that are not agonists of the $\beta_1$ and $\beta_2$ receptors can still modulate tachycardia through activation of a yet to be discovered $\beta_4$ or through some other unknown pathway.

A large number of publications have appeared in recent years reporting success in discovery of agents that stimulate the $\beta_3$ receptor. Despite these recent developments, there remains a need to develop a selective $\beta_3$ receptor agonist which has minimal agonist activity against the $\beta_1$ and $\beta_2$ receptors.

The present invention relates to a compound of formula I:

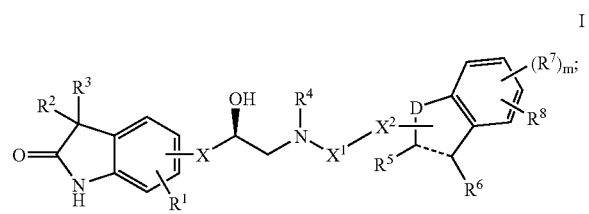

I wherein:
the dashed line represents a single or double bond;
m is 0, 1 or 2;
D is $NR^9$, O or S;

$R^1$ is H, CN, halo, $C_1$–$C_6$ alkyl, $C_1$–$C_4$ haloalkyl, $CO_2R^{10}$, $CONR^{10}R^{10}$, $NR^{10}COR^{10}$, $NR^{10}R^{10}R^{10}$, $SR^{10}$, $SOR^{10}$, $SO_2R^{10}$ or $SO_2NR^{10}R^{10}$;

$R^2$ is H, $C_1$–$C_6$ alkyl or benzyl;

$R^3$ is $C_1$–$C_6$ alkyl or benzyl;

or $R^2$ and $R^3$ combine with the carbon to which each are attached to form a $C_3$–$C_7$ carbocyclic ring; provided that if $R^3$ is $C_2$–$C_6$ alkyl or benzyl, then $R^2$ must be hydrogen;

$R^4$ is H or $C_1$–$C_6$ alkyl;

$R^5$ forms a bond with $X^2$ or is H, cyano, $C_1$–$C_6$, alkyl, $CONR^{11}R^{11}$ or $CO_2R^{11}$;

$R^6$ forms a bond with $X^2$ or is H or $C_1$–$C_6$ alkyl;

$R^7$ is independently at each occurrence halo, hydroxy, cyano, $C_1$–$C_6$ alkyl, $C_1$–$C_4$ haloalkyl or $C_1$–$C_6$ alkoxy;

$R^8$ is H, $CO_2R^{12}$, $CONR^{12}R^{12}$, $CH=CHR^{13}$, $CH_2CH_2R^{13}$, $NR^{12}R^{12}$, $NR^{12}SO_2R^{12}$, $O(CR^{14}R^{15})_nR^{16}$, $O(CR^{14}R^{15})_pR^{17}$, $SO_2R^{12}$, $SO_2NR^{12}R^{12}$, optionally substituted phenyl or optionally substituted heterocycle;

$R^9$ forms a bond with $X^2$ or is H or $C_1$–$C_6$ alkyl;

$R^{10}$, $R^{11}$ and $R^{12}$ are independently at each occurrence H, $C_1$–$C_6$ alkyl or phenyl; or when two $R^{10}$ or two $R^{11}$ or two $R^{12}$ moieties are connected to the same nitrogen atom, then said $R^{10}$ or $R^{11}$ or $R^{12}$ moieties may combine with the nitrogen to which they are attached to form a pyrollidinyl, piperidinyl or hexamethyleneimino ring;

$R^{13}$ is cyano, $CO_2R^{18}$, $CONR^{18}R^{18}$, $CONR^{18}SO_2R^{18}$, $SO_2R^{18}$, heterocycle or optionally substituted phenyl;

$R^{14}$ and $R^{15}$ are independently at each occurrence H or $C_1$–$C_6$ alkyl;

$R^{16}$ is hydrogen, $CO_2R^{19}$, $CONR^{19}R^{19}$, $SO_2R^{19}$, $SO_2NR^{19}R^{19}$, optionally substituted phenyl or optionally substituted heterocycle, $R^{17}$ is cyano, $NR^{20}R^{20}$, $NR^{20}SO_2R^{20}$ or $OR^{20}$;

$R^{18}$, $R^{19}$ and $R^{20}$ are independently at each occurrence H, $C_1$–$C_6$ alkyl or phenyl; or when two $R^{18}$ or two $R^{19}$ or two $R^{20}$ moieties are connected to the same nitrogen atom, then said $R^{18}$ or $R^{19}$ or $R^{20}$ moieties may combine with the nitrogen to which they are attached to form a pyrollidinyl, piperidinyl or hexamethyleneimino ring;

n is 0, 1, 2 or 3;

p is 1, 2 or 3;

X is $OCH_2$, $SCH_2$ or a bond;

$X^1$ is a bond or $(CR^{21}R^{22})_q$;

$X^2$ is a bond, CO, $CONR^{23}$ or $NR^{23}CO$;

q is 1, 2, 3, 4 or 5;

$R^{21}$ and $R^{22}$ are independently at each occurrence H or $C_1$–$C_6$ alkyl; or $R^{21}$ and $R^{22}$ combine with the carbon to which they are both attached to form a $C_3$–$C_7$ carbocyclic ring; and $R^{23}$ is H or $C_1$–$C_6$ alkyl; or a pharmaceutical salt thereof.

The present invention also relates to processes for preparing, as well as novel pharmaceutical formulations containing, a compound of formula 1. In another embodiment, the pharmaceutical formulations of the present invention may be adapted for use in treating Type 2 diabetes and obesity and for agonizing the $\beta_3$ receptor.

The present invention also relates to methods for treating Type 2 diabetes and obesity, as well as a method for agonizing the $\beta_3$ receptor employing a compound of formula I.

In addition, the present invention relates to a compound of formula I for use in treating Type 2 diabetes and obesity as well as a compound of formula I for use in agonizing the $\beta_3$ receptor. The present invention is further related to the use of a compound of formula I for the manufacture of a medicament for treating Type 2 diabetes and obesity as well as for agonizing the $\beta_3$ receptor.

For the purposes of the present invention, as disclosed and claimed herein, the following terms are defined below.

The term "halo" represents fluoro, chloro, bromo, or iodo.

The term "$C_1$–$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. The term "$C_1$–$C_4$ alkyl" refers specifically to methyl, ethyl, n-propyl, isopropyl, cyclopropyl, n-butyl, isobutyl, sec-butyl, t-butyl and cyclobutyl. A "$C_1$–$C_4$ haloalkyl" group is a $C_1$–$C_4$ alkyl moiety substituted with up to six halo atoms, preferably one to three halo atoms. An example of a haloalkyl group is trifluoromethyl. A "$C_1$–$C_6$ alkoxy" group is a $C_1$–$C_6$ alkyl moiety connected through an oxy linkage.

The term "optionally substituted" as used herein means an optional substitution of one to three, preferably one or two groups independently selected from halo, hydroxy, oxo, cyano, nitro, phenyl, benzyl, triazole, tetrazole, 4,5-dihydrothiazole, $C_1$–$C_6$ alkyl, $C_1$–$C_4$ haloalkyl, $C_1$–$C_6$ alkoxy, $COR^{24}$, $CONR^{24}R^{24}$, $CO_2R^{24}$, $NR^{24}R^{24}$, $NR^{24}COR^{25}$, $NR^{24}SO_2R^{25}$, $OCOR^{25}$, $OCO_2R^{24}$, $OCONR^{24}R^{24}$, $SR^{24}$, $SOR^{25}$, $SO_2R^{25}$ and $SO_2(NR^{24}R^{24})$, where $R^{24}$ is independently at each occurrence H, $C_1$–$C_6$ alkyl, phenyl or benzyl and $R^{25}$ is independently at each occurrence $C_1$–$C_6$ alkyl, phenyl or benzyl.

The term "heterocycle" represents a stable, saturated, partially unsaturated, fully unsaturated or aromatic 5 or 6 membered ring, said ring having from one to four heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine,,pyrrole, pyrrolidine, tetrazole, thiadiazole, thiazole, thiophene and triazole.

The term "suitable solvent" refers to any solvent, or mixture of solvents, inert to the ongoing reaction that sufficiently solubilizes the reactants to afford a medium within which to effect the desired reaction.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The preferred patient of treatment is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is capable of treating conditions, or detrimental effects thereof, described herein or that is capable of agonizing the $\beta_3$ receptor.

The term "selective $\beta_3$ receptor agonist" means a compound that displays preferential agonism of the $\beta_3$ receptor over agonism of the $\beta_1$ or $\beta_2$ receptor. Thus, $\beta_3$ selective compounds behave as agonists for the $\beta_3$ receptor at lower concentrations than that required for similar agonism at the $\beta_1$ and $\beta_2$ receptors. A $\beta_3$ selective compound also includes compounds that behave as agonists for the $\beta_3$ receptor and as antagonists for the $\beta_1$ and $\beta_2$ receptors.

The term "pharmaceutical" when used herein as an adjective means substantially non-deleterious to the recipient patient.

The term "formulation", as in pharmaceutical formulation, is intended to encompass a product comprising the active ingredient(s) (compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "unit dosage form" refers to physically discrete units suitable as unitary dosages for human subjects and other non-human animals (as described above), each unit containing a predetermined quantity of active material calculated to produce the desired therapeutic effect, in association with a suitable pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. Preferred acid addition salts include the hydrochloride and glycolate salts.

PREFERRED COMPOUNDS OF THE INVENTION

Certain compounds of the invention are particularly interesting and are preferred. The following listing sets out several groups of preferred compounds. It will be understood that each of the listings may be combined with other listings to create additional groups of preferred compounds.

a) the bond represented by a dashed line represents a double bond;
b) m is 0 or 1;
c) m is 0;
d) D is NH, O or S;
e) D is NH;
f) $R^1$ is H, methyl, ethyl, $CF_3$, chloro or fluoro;
g) $R^1$ is H, methyl, chloro or fluoro;
h) $R^1$ is H or fluoro;
i) $R^1$ is H;
j) $R^2$ and $R^3$ are both methyl;
k) $R^2$ and $R^3$ combine with the carbon to which each are attached to form a butacyclic or pentacylic ring;
l) $R^2$ and $R^3$ combine with the carbon to which each are attached to form a pentacylic ring;
m) $R^4$ is H;
n) $R^5$ is H;
o) $R^6$ forms a bond with $X^3$;
p) $R^7$ is fluoro or cyano;
q) $R^8$ is at the 7-position of the indole, benzofuran or benzothiophene ring system to which it is attached;
r) $R^8$ is H or $CO_2H$;
s) $R^8$ is $CH=CHR^{13}$, $R^{13}$ is phenyl substituted once with $SO_2NR^{24}R^{24}$ and $R^{24}$ is independently H or $C_1$–$C_4$ alkyl at each occurrence;
t) $R^8$ is $CH_2CH_2R^{13}$, $R^{13}$ is cyano; $CO_2H$; $CONR^{18}R^{18}$; $CO_2(C_1$–$C_4$ alkyl) or $SO2(C_1$–$C_4$ alkyl), and $R^{18}$ is independently H or $C_1$–$C_4$ alkyl at each occurrence;
u) $R^8$ is $CH_2CH_2R^{13}$, $R^{13}$ is 1,2,4-triazole; 1,2,3,4-tetrazole; pyrazine or phenyl substituted once with $SO_2NR^{24}R^{24}$ and $R^{24}$ is independently H or $C_1$–$C_4$ alkyl at each occurrence;
v) $R^8$ is thienyl substituted once with $CO_2H$ or phenyl substituted once or twice independently with $CO_2H$, $CF_3$, $CO(C_1$–$C_4$ alkyl), or $CO_2(C_1$–$C_4$ alkyl);
w) $R^8$ is $OCH_2CONHSO_2(C_1$–$C_4$ alkyl); $OCH_2CH_2NHSO_2(C_1$–$C_4$ alkyl); $OCH_2CN$; $OCH_2CO_2H$; O(pyridine) wherein said pyridine moiety is substituted once with cyano, $CO_2H$ or tetrazole; or $OCH_2(4,5$-dihydrothiazole);
x) $R^8$ is $NHSO_2R^{12}$ and $R^{12}$ is $C_1$–$C_4$ alkyl or phenyl;
y) $R^8$ is H;
z) $R^8$ is $CH_2CH_2R^{13}$ and $R^{13}$ is $CO_2H$;
aa) $R^8$ is $CH_2CH_2R^{13}$ and $R^{13}$ is 1,2,3,4-tetrazole or pyrazine;
bb) $R^8$ is phenyl substituted once with $CO_2H$;
cc) $R^8$ is $OCH_2CONHSO_2(C_1$–$C_4$ alkyl); $OCH_2CH_2NHSO_2(C_1$–$C_4$ alkyl); $OCH_2CO_2H$; O(pyridine) wherein said pyridine moiety is substituted once with cyano, $CO_2H$ or tetrazole; or $OCH_2(4,5$-dihydrothiazole);
dd) $R^8$ is $NHSO_2R^{12}$ and $R^{12}$ is phenyl;
ee) $R^9$ is H;
ff) X is $OCH_2$ and is connected through the 4-position of the indole ring (as shown in all of the exemplified compounds herein);
gg) $X^1$ is $(CR^{21}R^{22})_q$ where $R^{21}$ and $R^{22}$ are independently H or methyl at each occurrence and q is 2;
hh) $X^1$ is $C(CH_3)_2CH_2$;

ii) $X^2$ is a bond;
jj) the compound of formula I is an acid addition salt;
kk) the compound of formula I is the hydrochloride salt;
ll) the compound of formula I is the glycolate salt.

Synthesis

The compound of formula I may be prepared as described in the following Schemes and Examples.

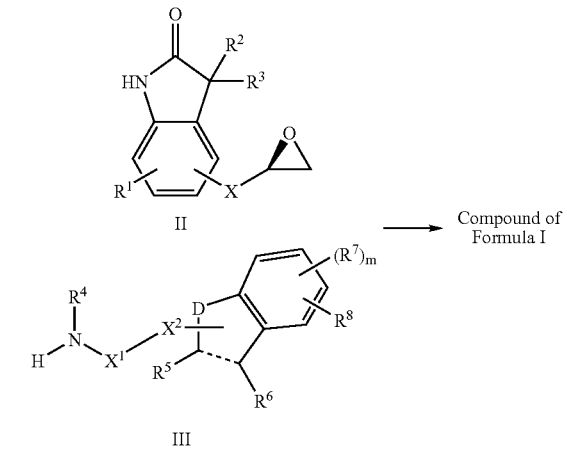

Scheme 1

The reaction of Scheme 1 may be carried out under conditions appreciated in the art for the amination of epoxides. For example, the epoxide of formula II may be combined with an amine of formula III in a lower alcohol, dimethylformamide, dimethylsulfoxide, or acetone, preferably ethanol, isopropanol, n-butanol or t-butanol, at room temperature to the reflux temperature of the reaction mixture, preferably between 40° C.–90° C. The reaction may also be carried out under conditions generally described in Atkins, et al., *Tet. Let.*, 27:2451, 1986. These conditions include mixing the reagents in the presence of trimethylsilyl acetamide in a polar aprotic solvent such as acetonitrile, dimethylformamide, acetone, dimethylsulfoxide, dioxane, diethylene glycol dimethyl ether, tetrahydrofuran, or other polar aprotic solvents in which the reagents are soluble. The epoxide starting materials employed in Scheme 1 may be prepared by techniques recognized and appreciated by one skilled in the art. See, e.g., references cited below in the Preparations section for representative and/or analogous procedures for preparing the epoxides of formula II. To illustrate, epoxides of formula II, where X is $OCH_2$ or $SCH_2$ and where $R^2$ and $R^3$ combine with the carbon to which each are attached to form a $C_3$–$C_7$ carbocyclic ring, may be prepared according to the procedure detailed in Scheme 2 wherein $R^{26}$ is chloro, bromo or iodo, X' is O or S, X" is $OCH_2$ or $SCH_2$ and r is 0–4.

In addition, epoxides of formula II, where X is $OCH_2$ or $SCH_2$ and where $R^2$ and $R^3$ do not combine with the carbon to which each are attached to form a carbocyclic ring, may be prepared according to the procedure detailed in Scheme 3 below where $R^{2'}$ is $C_1$–$C_6$ alkyl or benzyl.

Scheme 2

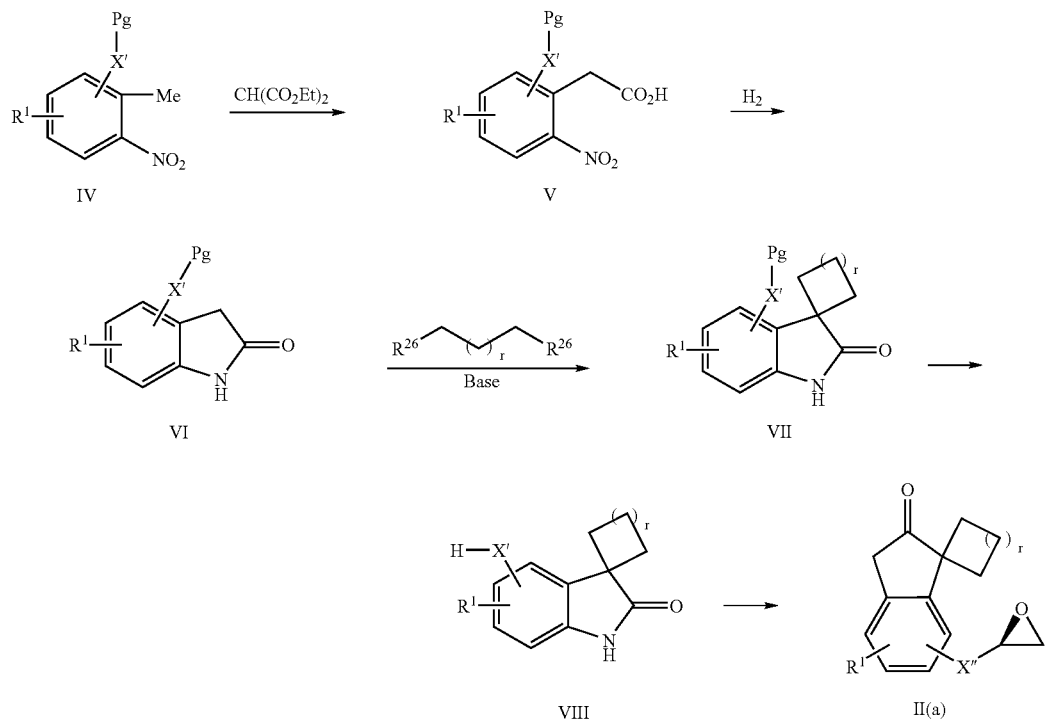

Scheme 3

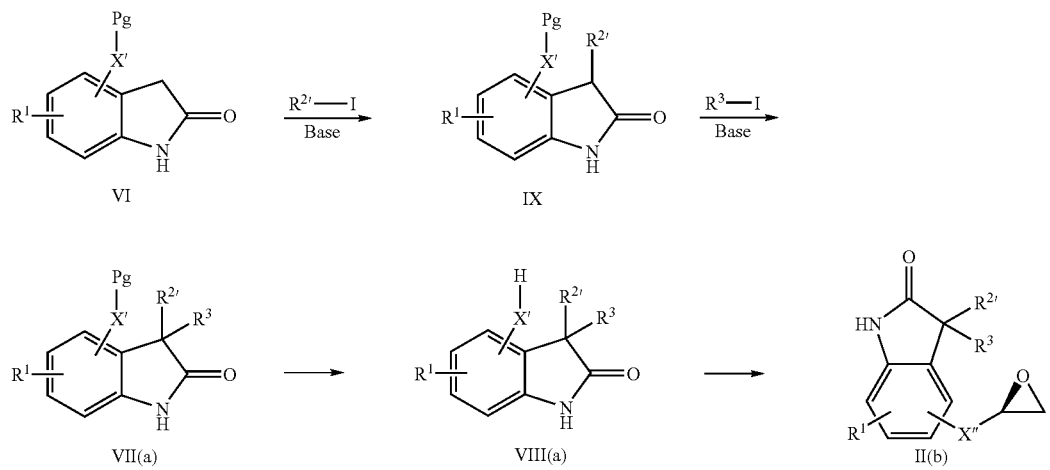

The compounds of formula II(a) and II(b) may be prepared by reacting equimolar amounts of a compound of formula VIII or VIII(a), respectively, with (2S)-(+)-glycidyl 3-nitrobenzenesulfonate. The reaction is typically performed in an inert solvent such as acetone and in the presence of a slight excess of a weak base, such as potassium carbonate. The suspension may then be heated at reflux for 16–20 hours with stirring to provide a compound of formula II(a) or II(b).

The cyclopropyl derivatives are prepared by a slightly modified procedure which involves treating the O- and N-diacetylated oxindole with 1,2 dibromoethane and potassium carbonate in dimethylsulfoxide.

The amines of formula III employed in Scheme 1 may also be prepared by techniques recognized and appreciated by one skilled in the art. See, e.g., the Preparations below or the references cited therein for representative and/or analogous procedures for preparing the amines of formula III.

Compounds of formula $R^{2'}$-I, $R^3$-I, IV and

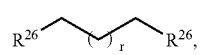

are either commercially available, known in the art, or can be prepared by methods known in the art or described herein.

Epoxides of Formula II

Epoxides 1–3 are prepared for use as described in Scheme 1. These epoxides are pictured below in Table 1.

TABLE I

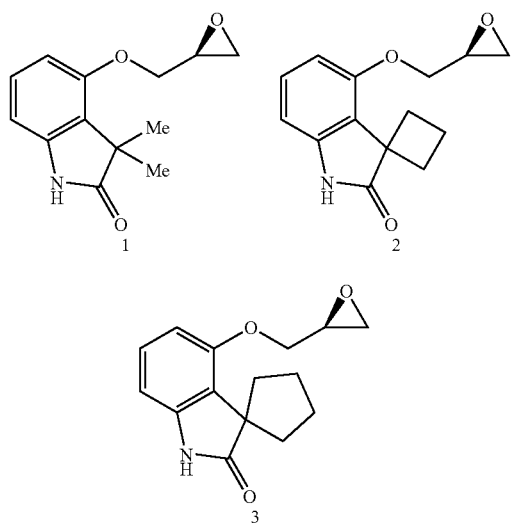

Epoxide 1

A solution of 4-methoxy-3-methyl-1,3-dihydro-indol-2-one (41.73 g, 235.5 mmol) and tetrahydrofuran (1000 mL) is cooled to −78° C. Potassium bis(trimethylsilyl)amide (989.0 mL, 494.3 mmol, 0.5 M in toluene) is added over 45 minutes so as to maintain the reaction temperature between −71° C. and −66° C. Iodomethane (36.71 g, 258.7 mmol) is added over 15 minutes between −75° C. and −70° C. The mixture is stirred at −78° C. for 1 hour then −60° C. for 30 minutes. Methanol (25 mL) is added at −60° C. Aqueous, hydrochloric acid (1N, 420 mL) is added rapidly allowing the temperature to rise to −7° C. The solution is transferred to a separatory funnel with aqueous hydrochloric acid (1N, 420 mL) and toluene (50 mL). The organic layer is extracted with a saturated sodium bicarbonate solution (250 mL), washed with a saturated sodium chloride solution (200 mL), dried over magnesium sulfate, and filtered. The filtrate is stirred with DARCO (25 g) for 1 hour then filtered. The filtrate is concentrated by rotary evaporation. The residue is refluxed for 1 hour in tert-butyl methyl ether (300 mL). After distilling out 100 mL of solvent, the slurry is stirred for 10 hours at 24° C. The solid is isolated by vacuum filtration rinsing twice with cold (−40° C.) tert-butyl methyl ether. After vacuum drying for 12 hours at 50° C./5 Torr, 23.9 g (58%) of 4-methoxy-3,3-dimethyl-1,3-dihydro-indol-2-one is obtained. mp 143–144° C. MS (ES+) m/z 192 ($M^+$+1).

Pyridine hydrochloride (51.10 g, 442.2 mmol) and 4-methoxy-3,3-dimethyl-1,3-dihydro-indol-2-one (21.61 g, 113.0 mmol) are combined and stirred in a melt at 220° C. for 45 minutes. Heating is removed and when the mixture cooled to 100° C., water (60 mL) is added, followed by ethyl acetate (150 mL) at 65° C. The layers are separated and the aqueous phase is extracted five times with ethyl acetate (50 mL). The combined organic layers are extracted first with a combination of aqueous hydrochloric acid (1N, 10 mL) and a saturated solution of sodium chloride (10 mL), then with a combination of a saturated solution of sodium bicarbonate (10 mL) and a saturated solution of sodium chloride (10 mL). After drying over magnesium sulfate, the solvent is removed via rotary evaporation. The crude material is dissolved in ethyl acetate (200 mL) and hexane (200 mL) at 60° C. Crystallization is allowed to begin slowly over 1 hour at 50° C. After stirring for 12 hours at 24° C., the slurry is cooled to 0° C. for 1 hour, then vacuum filtered washing twice with cold 1:1, ethyl acetate:hexane (35 mL, 0° C.) to provide 13.8 g (98.6% purity, 68% yield) of 4-hydroxy-3,3-dimethyl-1,3-dihydro-indol-2-one, mp 224–225° C. MS (ES+) m/z 178 ($M^+$+1). From the filtrate a second crop (5.0 g, 98.4% purity, 25% yield) is obtained to give a total yield of 93%.

Acetone (250 mL), 4-hydroxy-3,3-dimethyl-1,3-dihydro-indol-2-one (17.56 g, 99.1 mmol), powdered potassium carbonate (28.70.g, 208.1 mmol) and (2S)-(+)-glycidyl 3-nitrobenzenesulfonate (26.20 g, 101.1 mmol) are combined and the resulting mixture is refluxed for 22.5 hours. The solvent is removed by rotary evaporation and the crude material is purified by flash chromatography (500 g $SiO_2$; 1:1, ethyl acetate:hexane). During solvent removal from the product fractions, hexane (200 mL) is added and the product is crystallized in two crops. Isolation by vacuum filtration followed by vacuum drying at 50° C./5 Torr for 12 hours provided 11.0 g (47%) of the title epoxide, mp 156–158° C. MS (ES+) m/z 234 ($M^+$+1).

Epoxide 2

A suspension of 4-methoxy-1,3-dihydro-indol-2-one (3.7 g, 22.9 mmol) in tetrahydrofuran (110 mL) is cooled to −78° C. using a dry ice/acetone bath and treated with N,N,N',N'-tetramethylethylenediamine (8.6 mL, 57.1 mmol). N-butyllithium (36.0 mL, 57.1 mmol, 1.6 M in hexanes) is added dropwise, and the mixture stirred at this temperature for 30 minutes. 1,3 Diiodopropane (13.2 mL, 114.5 mmol) is added and the mixture is slowly warmed to room temperature and stirred for 18 hours. The reaction is quenched by addition of methanol (50 mL), followed by 1N aqueous hydrochloric acid to dissolve the resulting solids. The resulting mixture is partitioned-between ethyl acetate and brine. The aqueous phase is then extracted twice with ethyl acetate, and the combined organic phases are washed with brine, dried (magnesium sulfate), and concentrated. The crude material is preadsorbed on silica gel (15 g) and purified by flash chromatography (90 g silica gel, 15% ethyl acetate/hexane to 50% ethyl acetate/hexane with a linear gradient over 45 minutes to afford 1.55 g of 3-spirocyclobutane-4-methoxy-1,3-dihydro-indol-2-one (33%). MS (ESI+) 204.

To a solution of 3-spirocyclobutane-4-methoxy-1,3-dihydro-indol-2-one (1.55 g, 7.6 mmol) in dichloromethane (100 mL) at −78° C. is added dropwise a solution of boron tribromide in dichloromethane (1M, 38 mL, 38 mmol). After the mixture is stirred at −78° C. for 1 hour, the cooling bath is removed, and the mixture is allowed to warm to room temperature and stir overnight. The reaction is quenched by the addition of ice and water. The mixture is extracted three times with ethylacetate, and the combined organic phases are dried (magnesium sulfate), and concentrated. The crude material is preadsorbed on silica gel (7 g), and purified by flash chromatography (40 g silica gel, 25% ethylacetate:hexane to 60% ethylacetate:hexane, linear gradient over 45 minutes) to yield 750 mg (52%) of 3-spirocyclobutane-4-hydroxy-1,3-dihydro-indol-2-one. MS (ESI+) 190.

A mixture of 3-spirocyclobutane-4-hydroxy-1,3-dihydro-indol-2-one (1 equivalent), (2S)-glycidyl 3-nitrobenzenesulfonate (1.2 equivalents), potassium carbonate (1.2 equivalents) and acetone (resulting solution 0.2M in oxindole) is refluxed for 16 hours, cooled to room temperature and the solids removed via filtration. The filtrate is concentrated, redissolved in ethyl acetate and extracted several times with water. The organic layer is concentrated and the crude product either purified by flash chromatography (25% ethyl acetate/hexanes) or is used in the subsequent reactions without further purification. MS (ESI+) 246.

Epoxide 3

To a mixture of tetrahydrofuran (1000 mL) and 4-methoxy-1,3-dihydro-indol-2-one (48.30 g, 296.0 mmol) cooled to −65° C. was added N,N,N',N'-tetramethylethylenediamine (89.02 g, 766.0 mmol) maintaining the temperature between 65° C. and −63° C. After cooling further to −75° C., N-butyllithium (478.8 mL, 766.0 mmol, 1.6 M in hexanes) is added over 1 hour so as to maintain the temperature between −75° C. and −73° C. After stirring the mixture for 30 minutes at −72° C., 1,4-dibromobutane (330.82 g, 1.5321 mol) is added over 1 hour between −72° C. and −62° C. The solution is stirred at −33° C. for 15 hours then at 24° C. to 30° C. for 5 hours. Methanol (63 mL) is added to the mixture and the pH is adjusted to 6 with concentrated hydrochloric acid (50 mL), 3N aqueous hydrochloric acid (50 mL) and 1N aqueous hydrochloric acid (500 mL). Ethyl acetate (1000 mL) and a saturated solution of sodium chloride (300 mL) are added. The organic layer is separated and extracted with a combination of a saturated solution of sodium bicarbonate (500 mL) plus a saturated solution of sodium chloride (300 mL) then dried over magnesium sulfate. After filtration the solvent is removed by rotary evaporation at 44° C./5 Torr until no further distillate is obtained. Heptane (500 mL) is added and removed twice by rotary evaporation. Heptane (250 mL) is added and the mixture is stirred at 24° C. after which the solid is collected by vacuum filtration and rinsed three times with heptane (100 mL). After vacuum drying at 60° C./5 Torr for 14 hours, 53.1 g (94.3% purity, 78% yield) of 3-spirocyclopentane-4-methoxy-1,3-dihydro-indol-2-one is obtained as a solid, mp 168–169° C. MS (ES+) m/z 218 (M$^+$+1). From the filtrate a second crop (3.6 g, 96.3% purity, 6% yield) is obtained to give a total yield of 84%.

Alternatively, 3-spirocyclopentane-4-methoxy-1,3 dihydro-indol-2-one can be prepared as follows. A slurry of 4-methoxyindolin-2-one (200 g, 1.2 mol) and tetrahydrofuran (2.6 L) is cooled to −70° C. in a dry ice/acetone bath. A solution of sodium bis(trimethylsilyl)amide and tetrahydrofuran (4.9 L, 1M soln) pre-cooled to 4° C. is added to this slurry over 1.5 hours while maintaining a temperature of ≦−69° C. The resulting solution is maintained at this temp for 20 minutes post addition at which point 1,4 dichlorobutane (347 g, 2.7 mol) is added in one portion. The cooling bath is removed and the solution is allowed to warm to 30° C. over 4.5 hours. The solution is then heated to 35° C. for an additional 15.5 hours. Quenching is effected with methanol (260 mL) followed by water (3 L), and lastly, after installation of an ice bath, concentrated hydrochloric acid (640 mL) until the pH of the mixture is 2. The layers are separated and the aqueous layer is rinsed with ethylacetate (1.6 L), and the combined organic layers are washed with 1N aqueous hydrochloric acic/saturated sodium chloride (1.8 L/1.0 L). Again the aqueous layer is back-extracted with ethylacetate (1.2 L). The combined organic layers are rinsed with saturated sodium bicarbonate/saturated sodium chloride (1.2 L/1.2 L), dried (magnesium sulfate, 170 g) and filtered. The filtrate is then transferred to a rotary evaporator where a solvent exchange with heptane (4 L) is performed. When the slurry volume approaches 2 L it is cooled, filtered and dried in a 50° C. vacuum oven overnight to provide a granular orange solid (241.3, 91%) which is used without further purification.

Pyridine hydrochloride (127.6 g, 1.1042 mol) and 3-spirocyclopentane-4-methoxy-1,3-dihydro-indol-2-one (48.29 g, 0.2223 mol) are combined and stirred in a melt at 220° C. for 80 minutes. Heating is removed and at 100° C., water (150 mL) is added followed by ethyl acetate (300 mL) at 60° C. The layers are separated and the aqueous phase is extracted four times with ethyl acetate (100 mL). The combined organic layers are extracted first with a combination of aqueous hydrochloric acid (1N, 100 mL) and a saturated solution of sodium chloride (100 mL), then with a combination of a saturated solution of sodium bicarbonate (100 mL), a saturated solution of sodium chloride (100 mL), and water (200 mL). After drying over magnesium sulfate, the solvent is removed by rotary evaporation. The crude material is purified by flash chromatography (5 kg silica gel; 5.4% methanol, 43.3% heptane, 51.3% methylene chloride) to provide 38.7 g (85%) of 3-spirocyclopentane-4-hydroxy-1,3-dihydro-indol-2-one as a solid, mp 215–216° C. MS (ES+) m/z 204 (M$^+$+1).

Acetone (750 mL), 3-spirocyclopentane-4-hydroxy-1,3-dihydro-indol-2-one (37.76 g, 0.1858 mol), powdered potassium carbonate (53.92 g, 0.3901 mol) and (2S)-(+)-glycidyl 3-nitrobenzenesulfonate (50.57 g, 0.1951 mol) are combined and the resulting yellow mixture refluxed for 20 hours. After the solvent is removed by rotary evaporation, the resulting solid is dissolved in ethyl acetate (750 mL), water (2500 mL), and a saturated solution of sodium chloride (100 mL). The aqueous layer is separated and extracted with ethyl acetate (250 mL). The combined organic layers are extracted with a saturated solution of sodium chloride (200 mL), dried over sodium sulfate, and concentrated by rotary evaporation. The crude material is purified by flash chromatography (5 kg silica gel; 12 L of 3.0% methanol, 55.0% heptane, 42.0% methylene chloride; then 9 L of 5.0% methanol, 47.5% heptane, 47.5% methylene chloride). After vacuum drying at 50° C./5 Torr for 12 hours, 39.0 g (81%) of the title epoxide is obtained as a solid, mp 153–154° C. MS (ES+) m/z 260(M$^+$+1).

Amines of Formula III

Amines 1–88 are prepared or are obtained from commercial sources for use as described in Scheme 1. These amines are pictured below in Table 2.

TABLE 2
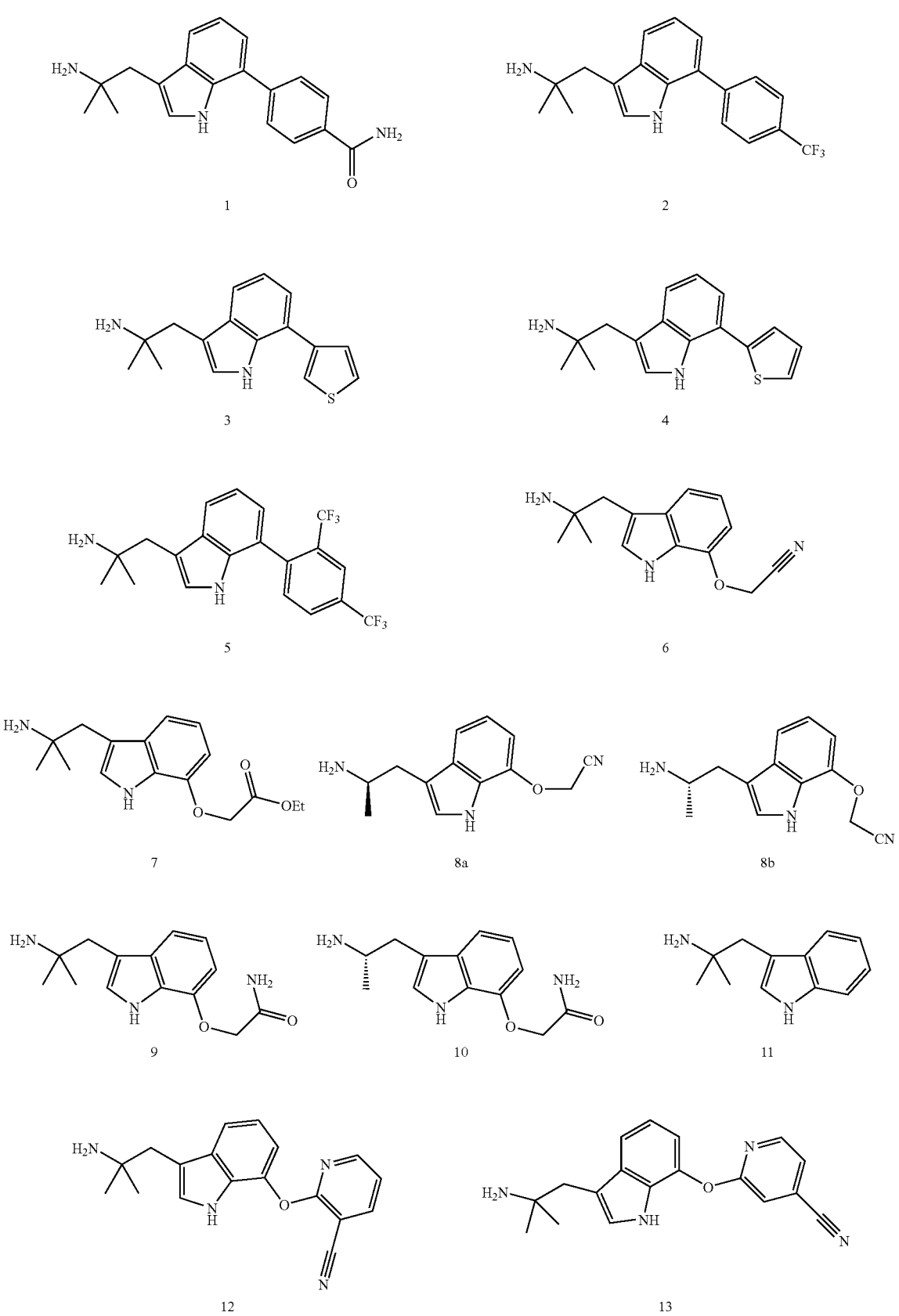

TABLE 2-continued
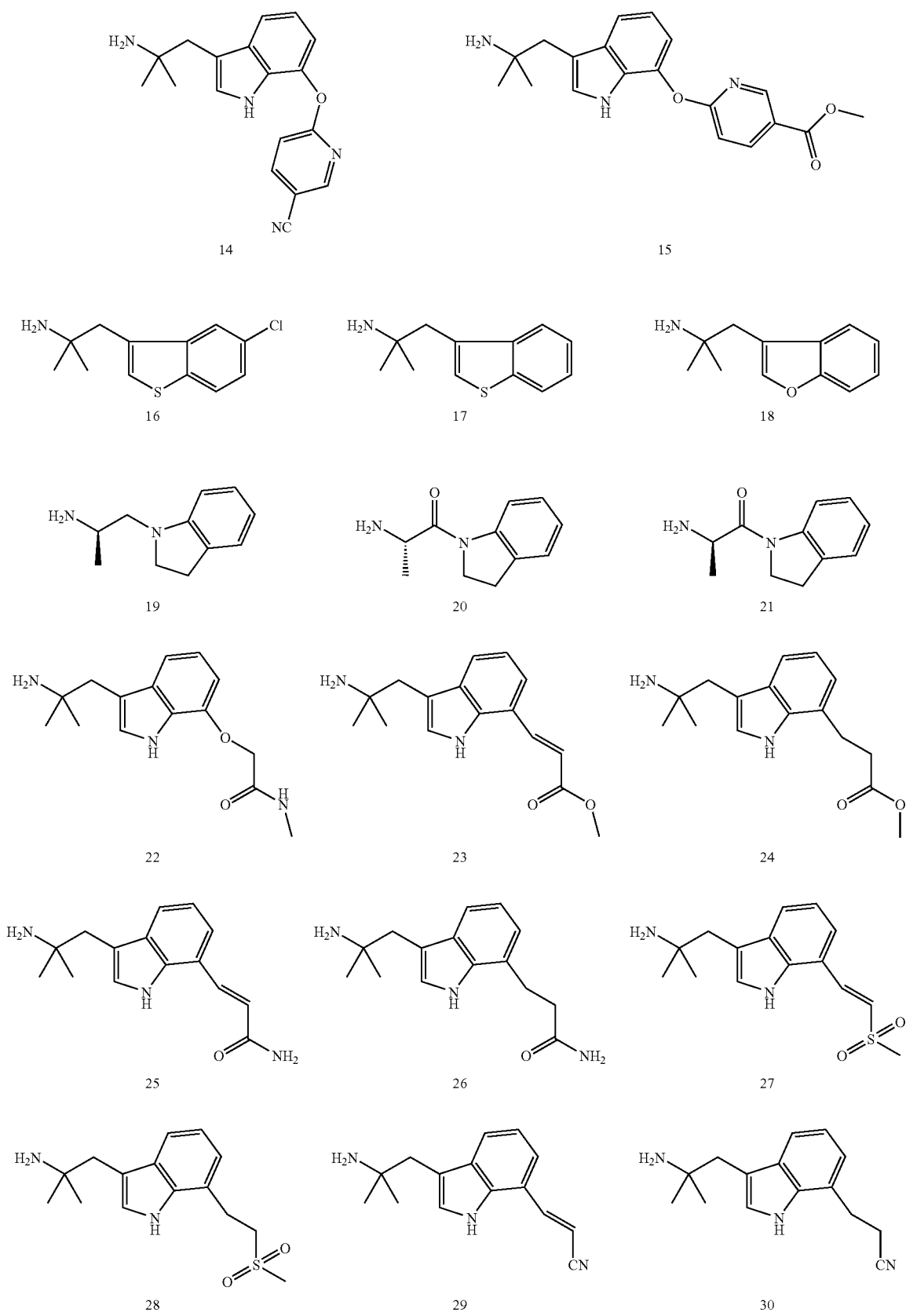

TABLE 2-continued
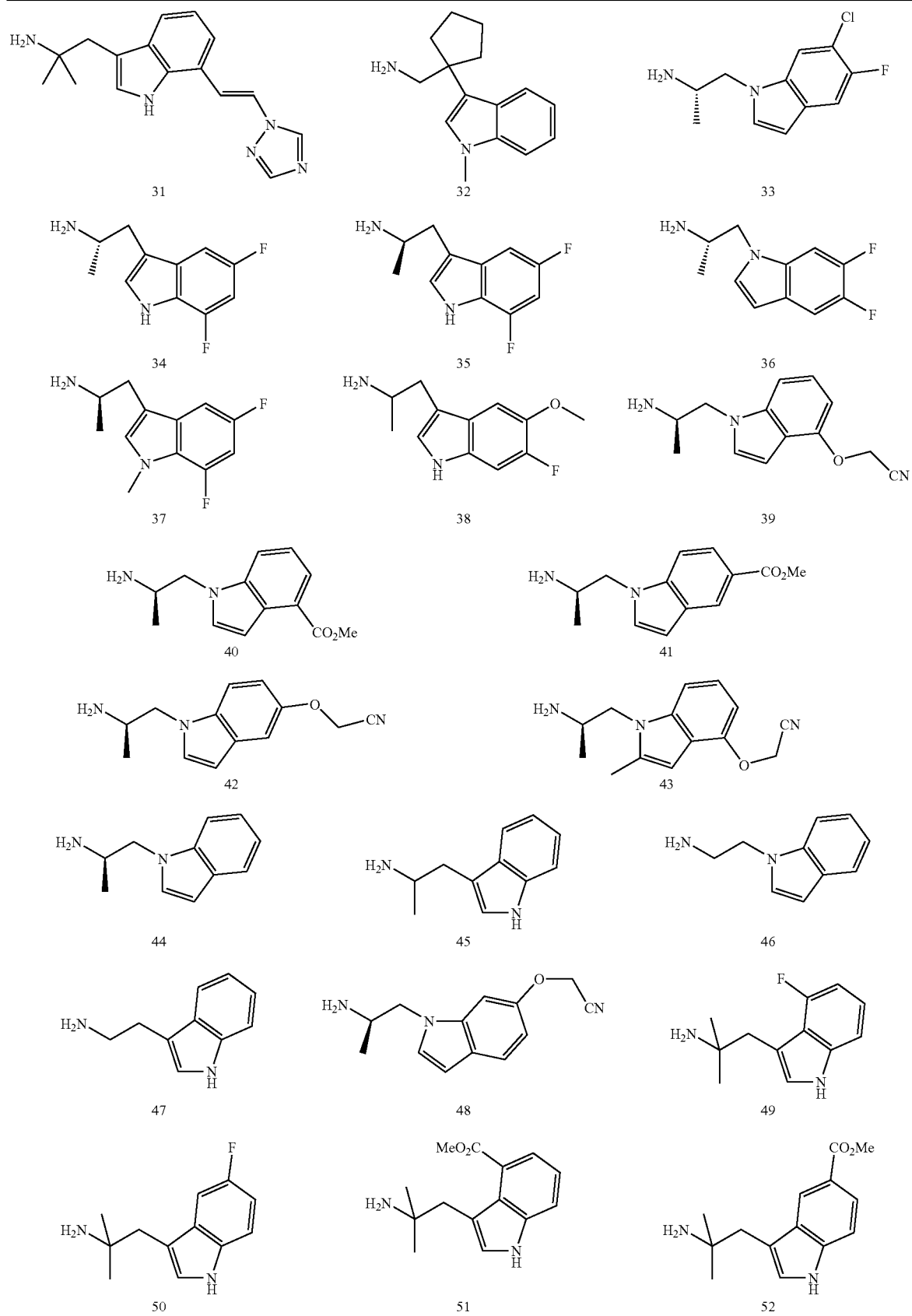

TABLE 2-continued

TABLE 2-continued
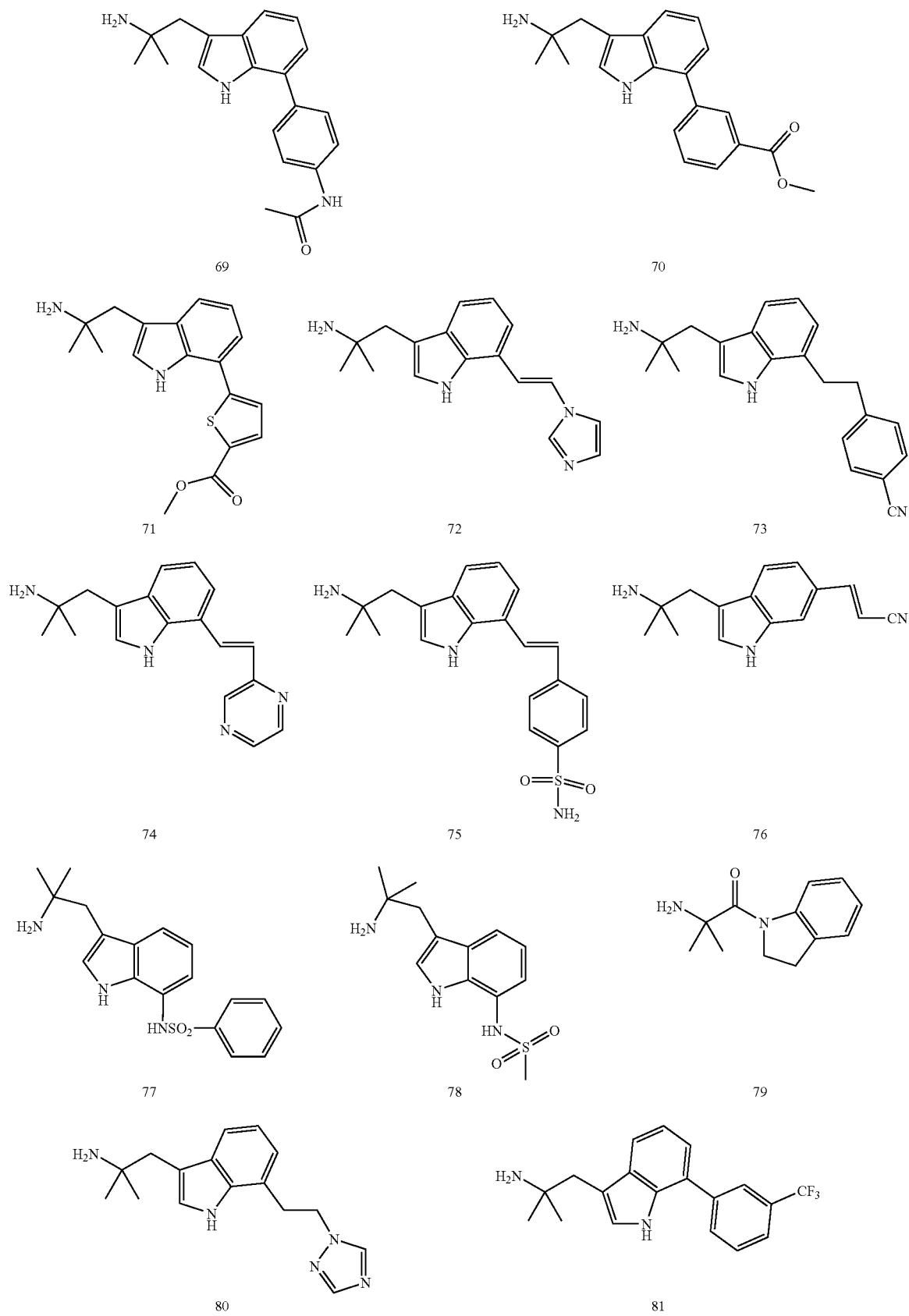

TABLE 2-continued

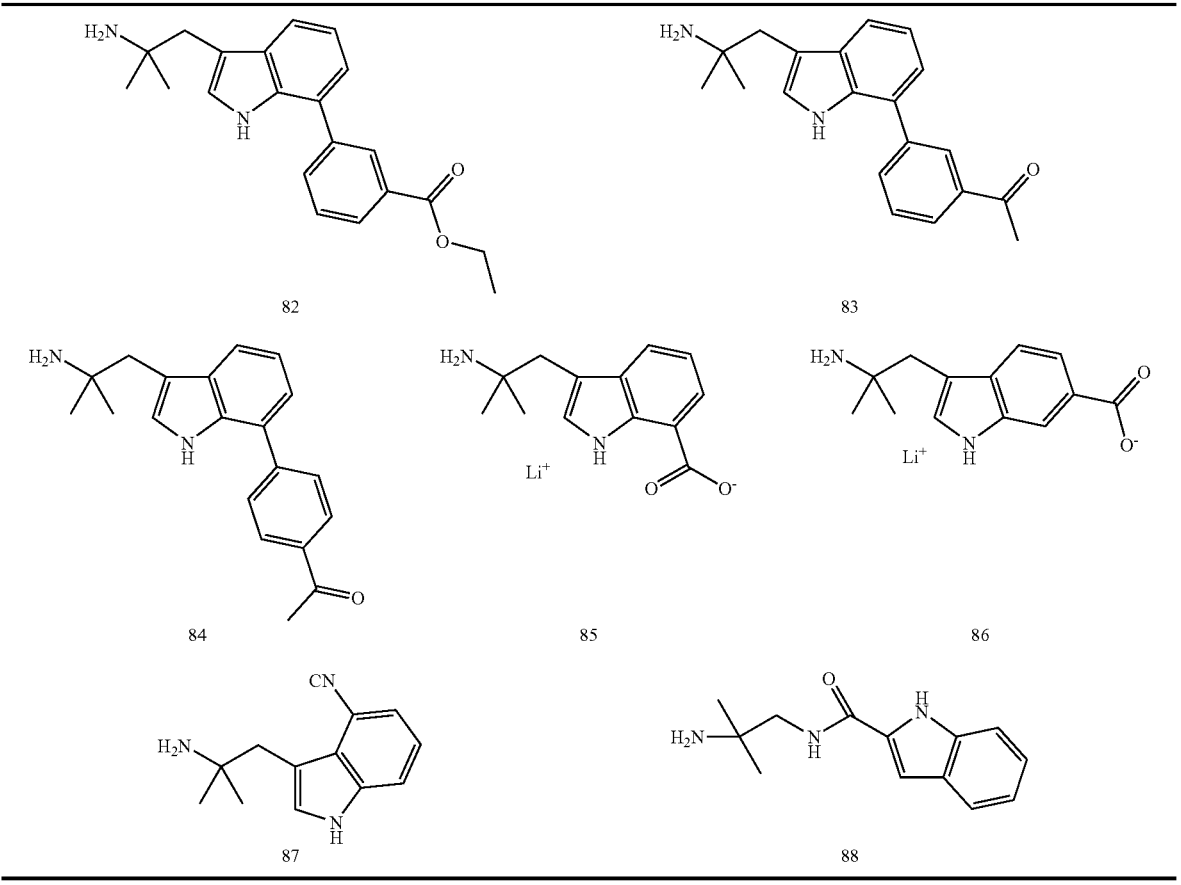

Amine 1

A mixture of 7-benzyloxy gramine (1.99 g, 7.10 mmol), solid NaOH (298 mg, 7.22 mmol) and 2-nitropropane (4.5 mL, 50 mmol) is heated to reflux. After 10 minutes at reflux, a thick slurry developed which is difficult to stir. Gas evolution is observed, and an additional 1 mL of 2-nitropropane is added to loosen the mixture. After 29 hours, the mixture is allowed to cool to ambient temperature. Ether (30 mL) is added and the mixture is filtered. The filtrate is treated with 10% acetic acid (6 mL), the layers are separated and the organic layer is rinsed with water (2×25 mL). The organic layer is dried ($Na_2SO_4$) and concentrated to give 2.12 g of 3-(2-methyl-2-nitropropyl)-7-(benzyloxy)indole (92%). MS (ES+) m/z 325.

A mixture of 3-(2-methyl-2-nitropropyl)-7-(benzyloxy) indole (25.0 g, 77.1 mmol), Raney Nickel® (9.5 g wet lump), and 3A ethanol (250 mL) is pressurized to 50 psig with $H_2$ and is heated to 60° C. After 1 hour, the mixture is cooled to ambient temperature. The mixture is diluted with tetrahydrofuran (100 mL) and is warmed to 50° C. The catalyst is removed by filtration and the cake is rinsed with 50° C. tetrahydrofuran (4×50 mL). The filtrate is concentrated to a solid which is dried in a 50° C. vacuum oven to provide 22.41 (99%) of 2-methyl-1-[7-(benzyloxy)indol-3-yl]prop-2-ylamine. MS (ES+) m/z 295 (100%).

Solid di-tert-butyl dicarbonate (20 g, 92 mmol) is added to a slurry of 2-methyl-1-[7-(benzyloxy)indol-3-yl]prop-2-ylamine (31.54 g, 107.1 mmol), triethylamine (16.5 mL, 118 mmol) and $CH_2Cl_2$ (300 mL) at ambient temperature; within 2 hours the slurry became a homogeneous solution. After 23.5 hours, the solution is poured into water (200 mL), and the layers are separated. The organic layer is extracted with 0.5 M $NaHSO_4$ (200 mL), and the combined aqueous layers are rinsed with $CH_2Cl_2$ (125 mL). The combined organic layers are rinsed with 50% saturated NaCl/saturated $NaHCO_3$ (300 mL), dried ($Na_2SO_4$), filtered and concentrated. The resulting residue is purified by flash chromatography with $CH_2Cl_2$ followed by 5% ethyl acetate/$CH_2Cl_2$ to provide 25 g of [2-(7-benzyloxy-1H-indol-3-yl)-1,1-dimethyl-ethyl]-carbamic acid tert-butyl ester (70%). MS (ES−) m/z 393 (100%).

A mixture of [2-(7-benzyloxy-1H-indol-3-yl)-1,1-dimethyl-ethyl]-carbamic acid tert-butyl ester (20.75 g, 52.6 mmol), 5% Pd/C (1.00 g, 5 wt %), and 3A ethanol (200 mL) is pressurized to 55 psig with $H_2$, and is heated to 50° C. After 40 minutes, the slurry is filtered, and the filtrate is concentrated to give 15.41 g of [2-(7-hydroxy-1H-indol-3-yl)-1,1-dimethyl-ethyl]-carbamic acid tert-butyl ester (96%). FDMS m/e=305 ($M^+$+1). To a solution of [2-(7-hydroxy-1H-indol-3-yl)-1,1-dimethyl-ethyl]-carbamic acid tert-butyl ester (6.04 g, 19.8 mmol) in dichloromethane (125 mL) is added triethylamine (14 mL, 99.2 mmol). The mixture is cooled to 0° C. and trifluoromethanesulfonyl anhydride (4.4 mL, 25.8 mmol) is added dropwise as a solution in dichloromethane (25 mL). The mixture is warmed to ambient and stirred overnight. The solution is diluted with brine and extracted three times with dichloromethane. The combined organics are dried over anhydrous sodium sulfate then filtered and evaporated. The residue is purified using silica gel chromatography (hexane/20% ethyl acetate in hexane gradient elution) to give 7.199 g of trifluoro-methanesulfonic acid 3-(2-tert-butoxycarbonylamino-2-methyl-propyl)-1H-indol-7-yl ester (83%). FDMS m/e=437 (M$^+$+1).

A solution of 4-bromobenzamide (150 mg, 0.75 mmol), bis(pinacolato)diboron (209 mg, 0.825 mmol), potassium acetate (0.221 g, 2.25 mmol) and {1,1'-bis(diphenylphosphino)-ferrocene}dichloropalladium dichloromethane complex (18 mg, 0.0225 mmol) in dimethylsulfoxide (5 mL) is heated to 80° C. for two hours. The mixture is cooled to 20° C. and trifluoro-methanesulfonic acid 3-(2-tert-butoxycarbonylamino-2-methyl-propyl)-1H-indol-7-yl ester (262 mg, 0.600 mmol), {1,1'-bis(diphenylphosphino)-ferrocene}dichloropalladium dichloromethane complex (18 mg, 0.0225 mmol) and sodium carbonate (1.9 mL, 2M, 3.75 mmol) are added. The mixture is heated to 80° C. overnight. The mixture is diluted with brine and ethyl acetate. The organic fraction is washed seven times with brine, then dried over anhydrous sodium sulfate, filtered and evaporated. The residue is purified using silica gel chromatography (dichloromethane/10% methanol, 0.7M ammonia in dichloromethane gradient elution) to give 143 mg of {2-[7-(4-carbamoyl-phenyl)-1H-indol-3-yl]-1,1-dimethyl-ethyl}-carbamic acid tert-butyl ester (58%). FDMS m/e=408 (M$^+$+1).

To a solution of {2-[7-(4-carbamoyl-phenyl)-1H-indol-3-yl]-1,1-dimethyl-ethyl}-carbamic acid tert-butyl ester (333 mg, 0.817 mmol) in dioxane (5 mL) at 0° C. is added hydrochloric acid (4 mL, 4M solution in dioxane, 16 mmol). The mixture is stirred at 0° C. for three hours and then warmed to ambient for three hours. The mixture is diluted with saturated sodium bicarbonate and then extracted three times with ethyl acetate. The combined organics are dried over anhydrous sodium sulfate, filtered and then the solvent is removed in vacuo to give 208 mg of the title compound (83%). FDMS m/e=308 (M$^+$+1).

Amine 2

To a solution of trifluoro-methanesulfonic acid 3-(2-tert-butoxycarbonylamino-2-methyl-propyl)-1H-indol-7-yl ester (305 mg, 0.699 mmol) in tetrahydrofuran (4.5 mL) is added sodium carbonate (1 mL, 2M, 2 mmol), tetrakis(triphenylphosphine)-palladium (32 mg, 0.0280 mmol) and 4-trifluoromethylbenzeneboronic acid (0.1 99 g, 1.05 mmol). The mixture is refluxed for 22 hours, then cooled, diluted with brine and extracted three times with ethyl acetate. The combined organics are dried over anhydrous sodium sulfate, filtered and then evaporated in vacuo. The residue is purified using silica gel chromatography (hexane/20% ethyl acetate, hexane gradient elution) to give 282 mg of {1,1-dimethyl-2-[7-(4-trifluoromethyl-phenyl)-1 H-indol-3-yl]-ethyl}-carbamic acid tert-butyl ester (93%). FDMS m/e=433 (M$^+$+1).

The title amine is prepared from {1,1-dimethyl-2-[7-(4-trifluoromethyl-phenyl)-1H-indol-3-yl]-ethyl}-carbamic acid tert-butyl ester as described above for Amine 1 (205 mg, 99%). FDMS m/e=333 (M$^+$+1).

Amine 3

To a solution of trifluoro-methanesulfonic acid 3-(2-tert-butoxycarbonylamino-2-methyl-propyl)-1H-indol-7-yl ester (340 mg, 0.779 mmol) in dimethylformamide (5 mL) is added triethylamine (0.14 mL, 1.01 mmol), tetrakis(triphenylphosphine)-palladium (36 mg, 0.0312 mmol) and 3-thiopheneboronic acid (130 mg, 1.01 mmol). The mixture is refluxed for. 22 hours, then cooled and diluted with brine and ethyl acetate. The organic phase is washed 7 times with brine. The organics are dried over anhydrous sodium sulfate, filtered and then evaporated in vacuo. The residue is purified using silica gel chromatography (hexane/20% ethyl acetate, hexane gradient elution) to give 198 mg of [1,1-dimethyl-2-(7-thiophen-3-yl-1H-indol-3-yl)-ethyl]-carbamic acid tert-butyl ester (69%). FDMS m/e=371 (M$^+$+1).

The title amine is prepared from [1,1-dimethyl-2-(7-thiophen-3-yl-1H-indol-3-yl)-ethyl]-carbamic acid tert-butyl ester as described above for Amine 1 (132 mg, 95%). FDMS m/e=271 (M$^+$+1).

Amine 4

To a solution of trifluoro-methanesulfonic acid 3-(2-tert-butoxycarbonylamino-2-methyl-propyl)-1H-indol-7-yl ester (437 mg, 1.00 mmol) in dimethylformamide (6 mL) is added triethylamine (0.18 mL, 1.30 mmol), tetrakis(triphenylphosphine)-palladium (46 mg, 0.0401 mmol) and 2-thiopheneboronic acid (167 mg, 1.30 mmol). The mixture is refluxed for 22 hours, then cooled and diluted with brine and ethyl acetate. The organic phase is washed 7 times with brine. The organics are dried over anhydrous sodium sulfate, filtered and then evaporated in vacuo. The residue is purified using silica gel chromatography (hexane/20%.ethyl acetate, hexane gradient elution) to give 116 mg of [1,1-Dimethyl-2-(7-thiophen-2-yl-1H-indol-3-yl)-ethyl]-carbamic acid tert-butyl ester (31%). FDMS m/e=371 (M$^+$+1).

The title amine is prepared from [1,1-Dimethyl-2-(7-thiophen-2-yl-1H-indol-3-yl)-ethyl]-carbamic acid tert-butyl ester as described above for Amine 1 (120 mg, 95%). FDMS m/e=271 (M$^+$+1).

Amine 5

To a solution of trifluoro-methanesulfonic acid 3-(2-tert-butoxycarbonylamino-2-methyl-propyl)-1H-indol-7-yl ester (262 mg, 0.600 mmol) in dimethylformamide (3.5 mL) is added triethylamine (0.11 mL, 0.780 mmol), tetrakis(triphenylphosphine)-palladium (28 mg, 0.0240 mmol) and 2,4-bistrifluoromethylbenzeneboronic acid (201 mg, 0.780 mmol). The mixture is heated to 100° C. for 20 hours, then cooled, diluted with brine and ethyl acetate. The organics are washed seven times with brine then dried over anhydrous sodium sulfate, filtered and evaporated in vacuo. The residue is purified using silica gel chromatography (hexane/20% ethyl acetate, hexane gradient elution) to give 268 mg of {2-[7-(2,4-Bis-trifluoromethyl-phenyl)-1H-indol-3-yl]-1,1-dimethyl-ethyl}-carbamic acid tert-butyl ester (89%). FDMS m/e=501 (M$^+$+1).

The title amine is prepared from {2-[7-(2,4-Bis-trifluoromethyl-phenyl)-1H-indol-3-yl]-1,1-dimethyl-ethyl}-carbamic acid tert-butyl ester as described above for Amine 1 (208 mg, 100%). FDMS m/e=401 (M$^+$+1).

Amines 6 and 7

A mixture of [2-(7-hydroxy-1H-indol-3-yl)-1,1-dimethyl-ethyl]-carbamic acid tert-butyl ester (15.55 g, 51.1 mmol), bromoacetonitrile (10.7 mL, 153 mmol), K$_2$CO$_3$ (17.78 g, 128.6 mmol) and 2-butanone is heated to reflux. After 1 hour the mixture is allowed to cool and is filtered through celite. The filtrate is concentrated to an oil which is purified by flash chromatography with $CH_2Cl_2$ followed by 5% ethyl acetate/$CH_2Cl_2$ to give 15.18 g of [2-(7-cyanomethoxy-1H-indol-3-yl)-1,1-dimethyl-ethyl]-carbamic acid tert-butyl ester (86%). MS (ES−) m/z 342.

To a solution of [2-(7-cyanomethoxy-1H-indol-3-yl)-1,1-dimethylethyl]-carbamic acid tert-butyl ester in 20 ml dry ethanol is added 2 ml 10% HCl in ethanol and the mixture is stirred at room temperature for 2 days. The solvent is evaporated, the residue re-dissolved in ethanol and loaded on a SCX column. After washing with ethanol the product is eluted with 10% $NH_3$ in ethanol, evaporated and purified on a silica column eluting with $CH_2Cl_2$/10% $NH_3$ in ethanol from 99/1 to 90/10, to yield 231 mg of Amine 6 (34%) and 213 mg of Amine 7 (26%).

Alternate Preparation for Amine 6

To solution of [2-(7-cyanomethoxy-1H-indol-3-yl)-1,1-dimethyl-ethyl]-carbamic acid tert-butyl ester (1.0 g, 2.85 mmol) in dioxane (5.0 mL) at 0° C. is added 4 N HCl (3.0 mL). The reaction mixture is allowed to continue for 1 hour at 0° C. and warmed to room temperature. The reaction mixture is evaporated to dryness, the resulting residue is taken up with water (25.0 mL), and saturated $NaHCO_3$ (5.0 mL) is added. This aqueous mixture is extracted with ethyl acetate (2×50 mL). The combined organic extracts are washed with brine and dried ($Na_2SO_4$). Evaporated to dryness give 590 mg of the title amine (86%). FDMS m/e=244.1 ($M^+$+1).

Amines 8a and 8b

Phosphorous oxychloride (252 mL, 2.7 mol) is added dropwise over 15 minutes to precooled dimethylformamide (−10° C.) (1800 mL) while maintaining the temperature below −5° C. and the resulting solution is stirred for 1 hour at −10 to 0° C. A solution of 7-benzyloxyindole (502 g, 2.25 mmol) in dimethylformamide (900 mL) is added. dropwise while maintaining the temperature below 0° C. The cooling is removed and the resulting mixture is allowed to warm to room temperature and stir for 1 hour. After cooling to 0° C., 5 N NaOH (4.5 L) is added over 20 minutes at 0° C. to 5° C. The resulting mixture is heated at reflux for 30 minutes. Upon cooling to 10° C., the product precipitates. After stirring for 20 minutes, the product is filtered, washed thoroughly with water (4×1.5 L) and vacuum dried at 40° C. to give 574.5 g of 7-benzyloxy-3-carbanal-1H-indole (101.6%).

The crude aldehyde from above (570 g, 2.25 mol), ammonium acetate (173.4, 2.25 mol) and nitroethane (661.8 g, 8.8 mol) are added to xylenes (1.35 L). The heterogeneous mixture is heated at reflux under a Dean-Stark trap with 4A molecular sieves in the sleeve for 30 minutes without reflux return and 45 minutes with reflux return to remove water. When the reaction is complete the mixture is cooled to room temperature over 1 hour and is then cooled to 0° C. for 30 minutes. The solid product is collected by filtration and is washed sequentially with xylenes (1 L), water (1 L), and xylenes (1 L). Vacuum drying overnight at 40° C. affords 610 g (88%) of 7-benzyloxy-3-(2-nitroprop-1-enyl)-1H-indole (nitroolefin).

Lithium aluminum hydride (LAH, 24 g, 600 mmol) is added portionwise to dry tetrahydrofuran (1800 mL) at −5° C. to 5° C. A solution of the nitroolefin from above (61.6 g, 200 mmol) in tetrahydrofuran (1200 mL) is added to the LAH solution over 30 minutes while maintaining the temperature at −5° C. to 5° C. When the addition is complete, the reaction mixture is allowed to warm to 30° C. over 1.5 hours and is stirred at 25° C. to 35° C. for 2 hours. To complete the reaction, the mixture is heated to 60° C. for 30 minutes. After cooling to 0° C., the reaction is quenched by the sequential addition of water (30 mL), 5 N NaOH (30 mL), and water (100 mL) and the resulting mixture is stirred over the weekend. The aluminum salts are removed by filtration and the cake rinsed with tetrahydrofuran (500 mL). The combined filtrates are concentrated to give 47.6 g (55% purity corrected yield, approx 65% pure) of 7-benzyloxy-3-(2-aminopropyl)-1H-indole.

To 7-benzyloxy-3-(2-aminopropyl)-1H-indole (45.6 g, 65% pure, 102 mmol) is added dichloromethane (450 mL) and triethylamine (18.1 g, 179 mmol) to give a slurry. t-Butyloxycarbonyl anhydride (35.5 g, 163 mmol) is added portionwise to the mixture over 5 minutes and is rinsed into the flask with dichloromethane (50 mL). Carbon dioxide gas is evolved and the temperature increases from 23° C. to 31° C. Within 1 hour the reaction is complete and the solution is washed sequentially with 1 N HCl, water, and 10% saturated sodium chloride solution. The crude product is purified by silica gel chromatography (500 g silica gel) eluting with dichloromethane followed by 5% ethyl acetate/dichloromethane. Crystallization of the product containing fractions from ethyl acetate/hexanes affords 33.9 g (86% yield) of {1-methyl-2-[7-(benzyloxy)-1H-indol-3-yl]ethyl}-carbamic acid tert-butyl ester.

{1-Methyl-2-[7-(benzyloxy)-1H-indol-3-yl]ethyl}-carbamic acid tert-butyl ester (38.9 g, 102 mmol) is added to a slurry of 5% Pd/carbon (3.89 g of 50% water wet catalyst) in ethanol denatured with toluene (389 mL). The resulting mixture is pressurized with hydrogen (50 psig) and is heated to 50° C. while shaking in a Paar™ hydrogenation apparatus. The reaction is complete after 3 hours, the catalyst is removed by filtration and the solvent is removed by rotary evaporation to afford a nearly quantitative yield of the oxygen-sensitive {1-methyl-2-[7-hydroxy-1H-indol-3-yl]ethyl}-carbamic acid tert-butyl ester. The phenol is used immediately in the next step without purification.

The crude {1-methyl-2-[7-hydroxy-1H-indol-3-yl]ethyl}-carbamic acid tert-butyl ester from above (29.2 g, 102 mmol theory) is dissolved in methyl ethyl ketone (300 mL) and bromoacetonitrile (20.4 mL, 306 mmol) and potassium carbonate (33.8 g, 250 mmol) is added. The mixture is heated at 80° C. for 2 hours. The solids are removed by filtration, the cake is washed with methyl ethyl ketone, and the combined filtrates are concentrated by rotary evaporation. The crude product is purified by flash chromatography (500 g silica gel, eluted with 8×500 mL dichloromethane, 4×500 mL 5% ethyl acetate/dichloromethane, 6×500 mL 10% ethyl acetate/dichloromethane). The fractions containing product are concentrated and hexane is added to the solution to precipitate out the product affording 23.7 g (70.2% yield) of racemic {1-methyl-2-[7-cyanomethoxy-1H-indol-3-yl]ethyl}-carbamic acid tert-butyl ester.

The two enantiomeric compounds that make up racemic {1-methyl-2-[7-cyanomethoxy-1H-indol-3-yl]ethyl}-carbamic acid tert-butyl ester are separated by preparative chiral chromatography in quantitative yield. Analytical chromatographic conditions: ChiralPak AD (4.6 mm×250 mm), 60% 3A ethanol, 40% heptane, 1 mL/min, 245 nm.

To a solution of (R)-{1-methyl-2-[7-cyanomethoxy-1H-indol-3-yl]ethyl}-carbamic acid tert-butyl ester (1.2 mmol) in 10 ml dry ethanol is added 1 ml 10% HCl in ethanol and the mixture is stirred at room temperature for 2 days. The solvent is evaporated, the residue re-dissolved in ethanol and loaded on a SCX column. After washing with ethanol the product is eluted with 10% NH₃ in ethanol and evaporated to yield 220 mg of Amine 8a (80%) as a colourless oil. Amine 8b is prepared from (S)-{1-methyl-2-[7-cyanomethoxy-1H-indol-3-yl]ethyl}-carbamic acid tert-butyl ester by a procedure substantially similar to that described for amine 8a.

Amine 9

To a solution of [2-(7-cyanomethoxy-1H-indol-3-yl)-1,1-dimethyl-ethyl]-carbamic acid tert-butyl ester (2.8 mmol) in 10 ml dry dioxane is added 1 ml concentrated HCl and the mixture is stirred at room temperature overnight. The solvent is evaporated, the residue re-dissolved in ethanol and loaded on a SCX column. After washing with ethanol the product is eluted with 10% NH₃ in ethanol and evaporated to yield 667 mg of Amine 9 (91%).

Amine 10

To a solution of Amine 8b (1.4 mmol) in 5 ml dry dioxane is added 0.5 ml concentrated HCl and the mixture is stirred at room temperature overnight. The solvent is evaporated, the residue re-dissolved in ethanol and loaded on a SCX column. After washing with ethanol the product is eluted with 10% NH₃ in ethanol and evaporated to yield 320 mg of Amine 10 (92%).

Amine 11

Amine 11 is prepared according to the literature procedure detailed in *J. Med. Chem.*, 23:285–289, 1980.

Amine 12

To a solution of [2-(7-Hydroxy-1H-indol-3-yl)-1,1-dimethyl-ethyl]-carbamic acid tert-butyl ester (274 mg, 0.900 mmol) in dimethylformamide (15 mL) is added sodium hydride (26 mg, 1.07 mmol). The mixture is stirred at ambient temperature for 25 minutes under nitrogen. 2-Chloro-nicotinonitrile (187 mg, 1.35 mmol) is added and the mixture is heated in an oil bath to eighty degrees Celsius for 15 hours, under nitrogen. Water (50 ml) is added to quench the reaction and the mixture is extracted three times with 50 mL of ethyl acetate. The organic layers are combined and washed twice with 50 mL of 1.00 N sodium hydroxide. The organic layer is dried with sodium sulfate, filtered and the solvent evaporated. The residue is dissolved in dichloromethane and purified using silica gel chromatography (6% 2M ammonia in methanol, 94% dichloromethane used as mobile phase) to give 350 mg (96%) of {2-[7-(3-cyano-pyridin-2-yloxy)-1H-indol-3-yl]-1,1-dimethyl-ethyl}-carbamic acid tert-butyl ester. FDMS m/e=407 (M⁺+1).

{2-[7-(3-Cyano-pyridin-2-yloxy)-1H-indol-3-yl]-1,1-dimethyl-ethyl}-carbamic acid tert-butyl ester (119 mg, 0.293 mmol) is dissolved in 10 mL of 1,4 dioxane. The mixture is cooled to zero degrees Celsius in an ice/water bath. To the mixture is added 10 mL of 4N hydrochloric acid in 1,4 dioxane, and the resulting mixture is stirred at zero degrees, under nitrogen, for five hours. The solvent is evaporated, and the residue is taken up in water. The pH of the water is adjusted to 9 using sodium bicarbonate, and is extracted three times with 50 mL of ethyl acetate. The organic layers are combined, dried with sodium sulfate, filtered, and the solvent removed in vacuo to give 218 mg of the title amine (83%). FDMS m/e=307 (M⁺+1).

Amines 13 and 14

The title amines are prepared from [2-(7-hydroxy-1H-indol-3-yl)-1,1-dimethyl-ethyl]-carbamic acid tert-butyl ester and 2-chloro-isonicotinonitrile and [2-(7-hydroxy-1H-indol-3-yl)-1,1-dimethyl-ethyl]-carbamic acid tert-butyl ester and 6-chloro-nicotinonitrile, respectively, as described for the preparation of Amine 12.

Amine 15

To a solution of [2-(7-hydroxy-1H-indol-3-yl)-1,1-dimethyl-ethyl]-carbamic acid tert-butyl ester (104 mg, 0.342 mmol) in dimethylformamide (10 mL) is added sodium hydride (10 mg, 0.410 mmol). The mixture is stirred at ambient temperature for 30 minutes under nitrogen. 6-Chloro-nicotinic acid methyl ester (99 mg, 0.581 mmol) is added and the mixture is heated in an oil bath to eighty degrees Celsius for 15 hours, under nitrogen. The mixture is then heated an additional 5 hours at eighty-five degrees Celsius. Water (100 ml) is added to quench the reaction and the mixture is extracted three times with 50 mL of ethyl acetate. The organic layers are combined and washed twice with 50 mL of 1.00 N sodium hydroxide. The organic layer is dried with sodium sulfate, filtered and the solvent evaporated. The residue is dissolved in dichloromethane and purified using silica gel chromatography (6% 2M ammonia in methanol, 94% dichloromethane used as mobile phase) to give 87 mg (58%) of 6-[3-(2-tert-butoxycarbonylamino-2-methyl-propyl)-1H-indol-7-yloxy]-nicotinic acid methyl ester. FDMS m/e=440 (M⁺+1).

6-[3-(2-tert-Butoxycarbonylamino-2-methyl-propyl)-1H-indol-7-yloxy]-nicotinic acid methyl ester (87 mg, 0.198 mmol) is dissolved in 5 mL of 1,4 dioxane. The mixture is cooled to zero degrees Celsius in an ice/water bath. To the mixture is added 15 mL of 4N hydrochloric acid in 1,4 dioxane, and the mixture is stirred at zero degrees, under nitrogen, for five hours. The solvent is evaporated, and the residue is taken up in water. The pH of the water is adjusted to 10 using sodium bicarbonate, and is extracted three times with 50 mL of ethyl acetate. The organic layers are combined, dried with sodium sulfate, filtered, and the solvent removed in vacuo to give 24 mg of the title amine (36%). FDMS m/e=340 (M⁺+1).

Amine 16

The title amine is prepared from 3-(bromomethyl)-5-chlorobenzo[B]thiophene in a similar fashion as described in U.S. Pat. No. 4,321,398.

Amine 17

3-Methylbenzo[b]thiophene (9.9 g, 67 mmol) is heated in carbon tetrachloride (133 ml ) to near reflux in the presence of n-bromosuccinimide (11.9 g, 67 mmol, 1.0 eq.). 2,2'Azobisisobutyronitrile (2.2 g, 13.3 mmol, 0.2 eq.) is added and the resulting mixture is refluxed for two hours. After cooling, the reaction mixture is filtered through a glass-fritted funnel, and the filtrate is concentrated. The residue is triturated with petroleum ether and toluene to afford 6.42 g of 3-Bromomethylbenzo[b]thiophene (42%).

The title amine is prepared from 3-(bromomethyl)-benzo[B]thiophene in a similar fashion as described in U.S. Pat. No. 4,321,398.

Amine 18

The title amine is prepared from 3-(Bromomethyl)benzofuran (*J. Med. Chem.*, 40(17):2706–2725, 1997) in a similar fashion as described in U.S. Pat. No. 4,321,398.

Amine 19

A mixture of 2,3-dihydro-1H-indole (5.74 g, 48.2 mmol), and (S)-propylene oxide (2.8 g, 48.2 mmol) in ethanol (200 mL) is heated at reflux for 18 hours. The resulting mixture is cooled to room temperature, and evaporated to give a crude oil. The material is purified by flash chromatography (25% ethyl acetate/hexanes) to give 5.37 g (63%) of 2,3-dihydro-1-(2-hydroxypropyl)indole.

To a solution of 2,3-dihydro-1-(2-hydroxypropyl)indole (4.87 g, 27.5 mmol) in $CH_2Cl_2$ (150 mL) at 0° C., is added triethylamine (19.1 mL, 137.4 mmol), followed by methanesulfonyl chloride (4.24 mL, 54.9 mmol). The reaction is quenched after 10 minutes by addition of saturated $NaHCO_3$ solution. The reaction mixture is extracted with $CH_2Cl_2$, dried over $MgSO_4$ and evaporated. This crude material is taken up in dimethylformamide (150 ml), sodium azide added (3.57 g, 54.9 mmol), and the reaction mixture heated at 70° C. for 7 hours. Diethyl ether and water is added to the cooled reaction mixture, and the water layer extracted several times with diethyl ether. The organic extracts are combined, washed with brine several times, dried over $Na_2SO_4$, and concentrated. The residue is purified by flash chromatography (15% ethyl acetate/hexanes) to give 4.44 g (80%) of 2,3-dihydro-1-(2-azidopropyl)indole.

2,3-Dihydro-1-(2-azidopropyl)indole (3.93 g, 19.5 mmol) and triphenylphosphine (6.38 g, 24.3 mmol) is dissolved in tetrahydrofuran (350 mL) and water (526 microliters, 29.2 mmol) is added. The reaction mixture is heated at reflux for 8 hours, cooled to room temperature, and concentrated. This crude residue is diluted with methanol, and passed over a cation exchange column to remove the excess triphenyl phosphine and byproducts. Flash chromatography (90:10:1 $CH_2Cl_2$/methanol/$NH_4OH$) provides the 1.05 g of the title amine (31%).

Amine 20

To a mixture of Boc-L-alanine (5 g, 24.4 mmol), indoline (3.2 ml, 29 mmol), and N,N-diisopropylethylamine (9.2 mL, 53 mmol) in dimethylformamide (I 30 mL) is added EDC (6.1 g, 32 mmol) and hydroxybenzotriazole (3.9 g, 29 mmol). The resulting mixture is stirred at room temperature overnight. The mixture is partitioned between ethyl acetate and $H_2O$. The aqueous phase is extracted with ethyl acetate, and the combined organic phases are washed with brine, dried ($MgSO_4$), and concentrated. The residue is purified by trituration with hexane to give 6.1 g of the Boc-protected title amine (80%).

To a mixture of the Boc-protected amine from above (4.0 g, 13.8 mmol) in $CH_2Cl_2$ (20 mL) at 0° C. is added trifluoroacetic acid (5 mL). Additional trifluoroacetic acid (5 mL) is added after 1 hour and 2 hours. After 2.5 hours, the mixture is neutralized with a saturated aqueous solution of $NaHCO_3$. The aqueous phase is extracted with $CH_2Cl_2$ (2×), and the combined organic phases are dried ($MgSO_4$) and concentrated to provide 2.0 g (77%) of the title amine.

Amine 21

The title amine is prepared from Boc-D-alanine (5 g, 24.4 mmol) and indoline (3.2 ml, 29 mmol) by a procedure substantially similar to that described above for Amine 20.

Amine 22

To a solution of [2-(7-cyanomethoxy-1H-indol-3-yl)-1,1-dimethyl-ethyl]-carbamic acid tert-butyl ester (3.8 mmol) is added 2 N NaOH (10.0 mL, 20 mmol). The reaction mixture is reluxed for 2 hours. The reaction mixture is cooled to room temperature, evaporated to about 10 mL, acidified to pH 3.0 with 1 N HCl. The mixture is extracted with ethyl acetate (2×50 mL), the combined organic layer washed with brine and dried ($Na_2SO_4$). Evaporation to dryness afford [3-(2-tert-butoxycarbonylamino-2-methyl-propyl)-1H-indol-7-yloxy)-acetic acid (1.3 g, 95%). FDMS m/e=363.2 ($M^+$+1). To a solution of [3-(2-tert-butoxycarbonylamino-2-methyl-propyl)-1H-indol-7-yloxy]acetic acid (480 mg, 1.32 mmol) in dimethylformamide (5.0 mL) is added methyl amine (1.52 mL, 1.0 M in tetrahydrofuran, 1.52 mmol) and Bop reagents (670 mg, 1.52 mmol). The reaction mixture is stirred at room temperature for 3 hours before evaporation to dryness. The resulting residue is chromatographed (30% ethyl acetate/hexane) to give 500 mg of [1,1-dimethyl-2-(7-methylcarbamoylmethoxy-1H-indol-3-yl)-ethyl]-carbamic acid tert-butyl ester (75%). FDMS m/e=375.1 ($M^+$+1).

The title amine is prepared from [1,1-dimethyl-2-(7-methylcarbamoylmethoxy-1H-indol-3-yl)-ethyl]-carbamic acid tert-butyl ester as described for the alternate preparation of Amine 6 (66%). FDMS m/e=276.1 ($M^+$+1).

Amine 23

Trifluoro-methanesulfonic acid 3-(2-tert-butoxycarbonylamino-2-methyl-propyl)-1H-indol-7-yl ester (200 mg, 0.46 mmol), methyl acrylate (80 mg, 0.92 mmol) and triethylamine (0.40 mL, 3.0 mmol) is stirred in dimethylformamide (2.0 mL) at room temperature for 30 minutes. Dichlorobis (triphenylphosphine)palladium (31 mg, 0.045 mmol) is added, the reaction mixture is heated to 90° C. and allowed to stir overnight. The reaction is cooled to room temperature, poured into a separatory funnel containing ethyl acetate and brine (50 mL each) and the aqeous layer is extracted with ethyl acetate (50 mL). The combined organic layers are washed with brine, dried ($Na_2SO_4$) and evaporated. The residue is purified using silica gel chromatography (20% ethyl acetate/hexane) to give 140 mg of 3-[3-(2-tert-butoxycarbonylamino-2-methyl-propyl)-1H-indol-7-yl]-acrylic acid methyl ester (82%). FDMS mie =372.2 ($M^+$+1).

The title compound is prepared from 3-[3-(2-tert-butoxycarbonylamino-2-methyl-propyl)-1H-indol-7-yl]-acrylic acid methyl ester as described for the alternate preparation of Amine 6 (82%). PDMS m/e 277.2 ($M^+$+1).

Amine 24

3-[3-(2-tert-Butoxycarbonylamino-2-methyl-propyl)-1H-indol-7-yl]-propionic acid methyl ester is prepared from 3-[3-(2-tert-butoxycarbonylamino-2-methyl-propyl)-1H-indol-7-yl]-acrylic acid methyl ester as described below for the preparation of {2-[7-(2-methanesulfonyl-ethyl)-1H-indol-3-yl]-1,1-dimethyl-ethyl}-carbamic acid tert-butyl ester (80%). FDMS m/e=375.2 ($M^+$+1).

The title amine is prepared from 3-[3-(2-tert-Butoxycarbonylamino-2-methyl-propyl)-1H-indol-7-yl]-propionic acid methyl ester as described for the alternate preparation of Amine 6 (100%).

Amine 25

3-[3-(2-tert-Butoxycarbonylamino-2-methyl-propyl)-1H-indol-7-yl]-acrylamide is prepared from [1,1-dimethyl-2-(7-trifluoromethanesulfonylmethyl-1H-indol-3-yl)-ethyl]-carbamic acid tert-butyl ester and acrylamide as described for the preparation of Amine 23 (98%). FDMS m/e 356.2 (M$^+$+1).

The title amine is prepared from 3-[3-(2-tert-butoxycarbonylamino-2-methyl-propyl)-1H-indol-7-yl]-acrylamide as described for the alternate preparation of Amine 6 (83%). FDMS m/e=258.2 (M$^+$+1).

Amine 26

{2-[7-(2-Carbamoyl-ethyl)-1H-indol-3-yl]-1,1-dimethyl-ethyl}-carbamic acid tert-butyl ester is prepared from 3-[3-(2-tert-butoxycarbonylamino-2-methyl-propyl)-1H-indol-7-yl]-acrylamide as described for the preparation of Amine 28 (100%). FDMS m/e=360.2 (M$^+$+1).

The title amine is prepared from {2-[7-(2-carbamoyl-ethyl)-1H-indol-3-yl]-1,1-dimethyl-ethyl}-carbamic acid tert-butyl ester as described for the alternate preparation of Amine 6 (98%). FDMS m/e=260.2 (M$^+$+1).

Amine 27

{2-[7-(2-Methanesulfonyl-vinyl)-1H-indol-3-yl)-1,1-dimethyl-ethyl}-carbamic acid tert-butyl ester is prepared from [1,1-dimethyl-2-(7-trifluoromethanesulfonylmethyl-1H-indol-3-yl)-ethyl]-carbamic acid tert-butyl ester and methyl vinyl sulfone as described for the preparation of Amine 23 (98%). FDMS m/e=392.2 (M$^+$+1).

The title amine is prepared from {2-[7-(2-methanesulfonyl-vinyl)-1 H-indol-3-yl]-1,1-dimethyl-ethyl}-carbamic acid tert-butyl ester as described for the alternate preparation of Amine 6 (80%). FDMS m/e=293.2 (M$^+$+1).

Amine 28

To a solution of {2-[7-(2-methanesulfonyl-vinyl)-1H-indol-3-yl]-1,1-dimethyl-ethyl}-carbamic acid tert-butyl ester (0.40 g, 1.02,mmol) in methanol (20.0 mL) is added 10% Pd/C (0.10 g) in methanol (2.0 mL). The reaction mixture is purged with hydrogen and hydrogenation is carried out with a hydrogen balloon overnight. The reaction mixture is filtered and the filtrate is evaporated to dryness to give 320 mg of {2-[7-(2-methanesulfonyl-ethyl)-1H-indol-3-yl]-1,1-dimethyl-ethyl}-carbamic acid tert-butyl ester (80%). FDMS m/e=395.2 (M$^+$+1).

The title amine is prepared from {2-[7-(2-methanesulfonyl-ethyl)-1H-indol-3-yl]-1,1-dimethyl-ethyl}-carbamic acid tert-butyl ester as described for the alternate preparation of Amine 6 (92%). FDMS m/e=295.2 (M$^+$+1).

Amine 29

{2-[7-(2-Cyano-vinyl)-1H-indol-3-yl]-1,1-dimethyl-ethyl}-carbamic acid tert-butyl ester is prepared from [1,1-dimethyl-2-(7-trifluoromethanesulfonylmethyl-1H-indol-3-yl)-ethyl]-carbamic acid tert-butyl ester and acrylonitrile as described for the preparation of Amine 23 (85%). FDMS m/e=339.2 (M$^+$+1).

The title amine is prepared from {2-[7-(2-Cyano-vinyl)-1H-indol-3-yl]-1,1-dimethyl-ethyl}-carbamic acid tert-butyl ester as described for the alternate preparation of Amine 6 (94%). FDMS m/e=240.2 (M$^+$+1).

Amine 30

{2-[7-(2-Cyano-ethyl)-1H-indol-3-yl]-1,1-dimethyl-ethyl}-carbamic acid tert-butyl ester is prepared from {2-[7-(2-cyano-vinyl)-1H-indol-3-yl]-1,1-dimethyl-ethyl}-carbamic acid tert-butyl ester as described for the preparation of Amine 28 (86%). FDMS m/e=341.2 (M$^+$+1)

The title amine is prepared from {2-[7-(2-Cyano-ethyl)-1H-indol-3-yl]-1,1-dimethyl-ethyl}-carbamic acid tert-butyl ester as described for the alternate preparation of Amine 6 (86%). FDMS m/e=242.2 (M$^+$+1).

Amine 31

{1,1-Dimethyl-2-[7-(2-[1,2,4]triazol-1-yl-vinyl)-1H-indol-3-yl]-ethyl}-carbamic acid tert-butyl ester is prepared from [1,1-dimethyl-2-(7-trifluoromethanesulfonylmethyl-1H-indol-3-yl)-ethyl]-carbamic acid tert-butyl ester and I-vinyl-1,2,4-triazole as described for the preparation of Amine 23 (93%). FDMS m/e=381.2 (M$^+$+1).

The title amine is prepared from {1,1-dimethyl-2-[7-(2-[1,2,4]triazol-1-yl-vinyl)-1H-indol-3-yl]-ethyl}-carbamic acid tert-butyl ester as described for the alternate preparation of Amine 6 (56%). FDMS m/e=282.2 (M$^+$+1).

Amine 32

(1-Methyl-1H-indol-3-yl)-acetonitrile (*J. Org. Chem.*, 63:6053–6058, 1998) is converted to 1-(1-methyl-1H-indol-3-yl)-cyclopentanecarbonitrile and then said carbonitrile compound is converted to the title amine via procedures described in *Eur. J. Med. Chem.*, 31:123–132, 1996.

Amine 34

To a vigorously stirred solution of 2-bromo-4,6-difluoro aniline (100 g, 0.48 mol) in pyridine (400 mL), at 0° C., is added ethyl chloroformate (70 ml, 0.73 mol) at a rate to keep the temperature below 5° C. When addition is complete, the mixture is stirred at 0° C.–5° C. an additional 2 hours while monitoring by TLC (20% ethyl acetate/hexane, UV). The reaction is then allowed to warm to room temperature, filtered and the filtrate concentrated. The residue is dissolved in diethyl ether/ethyl acetate (500 ml/250 ml) and washed with $H_2O$, 2.5 N HCl, aqueous $NaHCO_3$, brine, dried ($Na_2SO_4$), filtered, concentrated, and triturated with petroleum ether to give 126 g of 2-bromo-4,6-difluoro-N-carbethoxy aniline (94%).

In a 2 L flask, 2-bromo-4,6-difluoro-N-carbethoxy aniline (42 g, 150 mmol) in $CH_3CN$ (500 mL) is degassed with vacuum and purged with $N_2$. Dichlorobis(triphenylphosphine)palladium(II) (10.5 g, 15 mmol, 10 mol %), followed by CuI (710 mg, 4 mmol, 2.5 mol %) and triethyl amine (41 mL) are added and rinsed in with 100 mL of $CH_3CN$. Trimethylsilyl acetylene (31.8 ml, 225 mmol) is added and reaction is refluxed under $N_2$. Approximately 2 hours later, the starting material is consumed, indicated by TLC (20% ethyl acetate/hexane, UV). The reaction is cooled, filtered, concentrated, and the residue is dissolved in ethyl acetate, washed with H$_2$O, brine, dried (Na$_2$SO$_4$), filtered, concentrated, and is purified by flash chromatography (SiO$_2$, ethyl acetate/hexane gradient) to yield 30 g of 2-(trimethylsilylethynyl)-4,6-difluoro-N-carbethoxyaniline (71%).

Fresh sodium ethoxide is prepared by carefully adding NaH (16 g of 60% oil dispersion, 400 mmol) to 550 mL of ethanol under N$_2$. 2-(Trimethylsilylethynyl)-4,6-difluoro-N-carbethoxyaniline (28 g, 100 mmol) in 150 mL of ethanol is added and reaction is stirred at room temperature approximately 45 minutes, while monitoring by TLC (20% ethyl acetate/hexane, UV) until all the starting material is consumed. The mixture is heated to reflux and monitored by TLC until the intermediate material is consumed (approx. 1 hour). Reaction is cooled to room temperature, concentrated, diethylether is added, washed with H$_2$O, brine, dried (Na$_2$SO$_4$), filtered, concentrated, and is purified by flash chromatography (SiO$_2$, ethyl acetate/hexane gradient) to yield 12 g of 5,7-difluoro-indole (78%).

The 1.0 M ICl in CH$_2$Cl$_2$ (43 ml, 43 mmol) is added to a solution of 5,7-difluoroindole (6 g, 39 mmol) in 35 ml pyridine under N$_2$ at 0° C. and the resulting mixture is stirred for 30 minutes. The reaction is diluted with toluene and washed with brine, 1N HCl, 1N NaOH, dried (Na$_2$SO$_4$), filtered and concentrated. The crude 3-iodo-5,7-difluoroindole is stirred in toluene (85 ml) and 5 N NaOH (70 ml), tetrabutylammonium bromide (1.25 g, 3.9 mmol), then benzenesulfonyl chloride (6.2 ml, 48 mmol) are added and the resulting mixture is stirred 24 hours. The two phase reaction mixture is diluted with toluene, washed with brine, dried(Na$_2$SO$_4$), filtered, concentrated and the residue is triturated with diethyl ether/petroleum ether. The resulting solid is filtered to give 14.2 g of N-Benzenesulfonyl-3-iodo-5,7-difluoroindole (87%).

A 3.0 M diethyl ether solution of ethylmagnesium bromide (7.3 ml, 21.8 mmol) is added under N$_2$ at 0° C. to a 95 ml tetrahydrofuran solution of N-benzenesulfonyl-3-iodo-5,7-difluoro-indole (8.4 g, 20 mmol). The resulting mixture is stirred for 20 minutes at 0° C., allowed to warm to room temperature over 20 minutes, then recooled to 0° C. A 20 ml tetrahydrofuran solution of (S) N,N dibenzyl-2-aminopropanal (*Syn. Lett.*, 1997,2, 223–224, 5.1 g, 22 mmol) is added to the reaction mixture and the resulting mixture is stirred 1 hour as it warmed to room temp. The reaction is quenched with aqueous NH$_4$Cl, extracted with ethyl acetate, washed with brine, dried (Na$_2$SO$_4$), filtered, concentrated, and the residue is purified by flash chromatography (SiO$_2$, ethyl acetate/hexane gradient) to yield 8.4 g of 2-(N,N-dibenzylamino)-1-(1-benzenesulfonyl-5i7-difluoro-1H-indol-3-yl)-propan-1-ol. (77%)

Lithium aluminum hydride (LAH) (0.7 g, 18 mmol) is added portionwise to a dioxane/tetrahydrofuran (90 ml/10 ml) solution of 2-(N,N-dibenzylamino)-1-(1-benzenesulfonyl-5,7-difluoro-1H-indol-3-yl)-propan-1-ol (1.9 g, 3.3 mmol) under N$_2$ at 0° C. After the addition is complete, the reaction is allowed to warm to room temperature, then is refluxed for 1 hour. The reaction is quenched with H$_2$O and 15% aqueous NaOH, filtered, and the filtrate is diluted with ethyl acetate, washed with brine, dried (Na$_2$SO$_4$), filtered, concentrated, and the residue is purified by flash chromatography (SiO$_2$, ethyl acetate/hexane gradient) to yield 1.2 g of dibenzyl-[2-(5,7-difluoro-1H-indol-3-yl)-1(S)-methyl-ethyl]-amine (86%).

A 100 ml ethanol mixture of dibenzyl-[2-(5,7-difluoro-1H-indol-3-yl)-1(S)-methyl-ethyl]-amine (930 mg, 2.4 mmol), ammonium formate (1.5 g, 24 mmol), and 10% palladium on charcoal (250 mg, 0.24 mmol) is reluxed 1 hour, cooled, filtered, and concentrated. The residue is purified by flash chromatography using a variable mixture of 90:10:1 CH$_2$Cl$_2$/methanol/NH$_4$OH to give 420 mg of the title amine (83%).

Amine 35

The title amine is prepared from N-benzenesulfonyl-3-iodo-5,7-difluoro-indole and (R) N,N dibenzyl-2-aminopropanal by a procedure substantially similar to that described for Amine 34.

Amines 33 and 36

The title amines are prepared as described in *J. Med. Chem.*, 40:2762–2769, 1997.

Amine 37

NaH (180 mg of 60% oil dispersion, 4.5 mmol) is added to a solution of dibenzyl-[2-(5,7-difluoro-1H-indol-3-yl)-1(R)-methyl-ethyl]-amine (1.4 g, 3.6 mmol) in 20 ml dimethylformamide under N$_2$ at 0° C. The resulting mixture is stirred for 20 minutes, then is allowed to warm to room temperature over 20 minutes. A 5 ml solution of iodomethane in dimethylformamide (7.2 mmol) is added dropwise and the reaction mixture is stirred for 1 hour. The reaction is quenched with cold aqueous NaHCO$_3$, extracted with ethyl acetate, washed with brine, dried (Na$_2$SO$_4$), filtered, concentrated and is purified by flash chromatography (SiO$_2$, ethyl acetate/hexane gradient) to yield 1.3 g of dibenzyl-[2-(5,7-difluoro-1-methyl-1H-indol-3-yl)-1(R)-methyl-ethyl]-amine (89%).

Dibenzyl-[2-(5,7-difluoro-1-methyl-1H-indol-3-yl)-1(R)-methyl-ethyl]-amine (1.23 g, 3 mmol) is deprotected in the same manner as Amine 34 to give 500 mg of the title amine (76%).

Amine 38

POCl$_3$ (10.9 ml, 71 mmol) is added dropwise to 21 ml of dimethylformamide under N$_2$ at 10–20° C., is stirred 15 minutes, then a 13 ml dimethylformamide solution of 5-methoxy-6-fluoro-indole (*J. Med. Chem.*, 22:63–69, 1979; 10.7 g, 64.7 mmol) is added at a rate to keep the reaction temperature between 10 and 20° C. After the addition is complete, the mixture is stirred for 1 hour. Crushed ice and aqeuous NaOH (12.5 g/50 ml H$_2$O) is added to reaction. The resulting mixture is heated to reflux with a heat gun for 1 minute, cooled to 10° C., and is filtered to give 11.8 g of 6-fluoro-5-methoxy-1H-indole-3-carbaldehyde (95%).

A mixture of nitroethane(44 ml, 611 mmol), 6-fluoro-5-methoxy-1H-indole-3-carbaldehyde (11.8 g, 61 mmol), and ammonium acetate(1.78 g, 23 mmol) is stirred at 100° C. for 3 hours, allowed to cool, and is filtered to give 14 g of 6-fluoro-5-methoxy-3-(2-nitro-propenyl)-1H-indole (92%).

A 45 ml tetrahydro solution of 6-fluoro-5-methoxy-3-(2-nitro-propenyl)-1H-indole (2.83 g, 11,3 mmol) is added dropwise to a 60 ml tetrahydrofuran suspension of LAH (2.14 g, 56.5 mmol) at 0° C., and the resulting mixture is allowed to warm to room temperature, then is refluxed for 1 hour. The reaction is quenched with H$_2$O and 15% aqueous NaOH, then is filtered, concentrated, and the filtrate is diluted with ethyl acetate, washed with brine, dried (Na$_2$SO$_4$), filtered, concentrated, and the residue is purified by flash chromatography (90:10:1 CH$_2$Cl$_2$/methanol/NH$_4$OH) to give I g of the title amine (41%).

Amine 39

A 0° C. solution of 4-hydroxyindole (20 g, 150 mmol) in 500 ml of dimethylformamide is treated with NaH (60% dispersion in mineral oil; 6.6 g, 165 mmol). After 30 minutes, bromoacetonitrile (11.5 ml, 165 mmol) is added, and the resulting mixture is allowed to slowly warm to ambient temperature and stir for 3 days. The reaction mixture is diluted with ethyl acetate and washed 3 times with $H_2O$. The organic layer is dried over $Na_2SO_4$ and concentrated in vacuo. The crude residue is purified by normal phase HPLC ($SiO_2$; 5% step gradient of 0 to 20% ethyl acetate in hexanes) to give 25 g of (1H-indol-4-yloxy)acetonitrile (97%).

A 0° C. solution of (1H-indol-4-yloxy)acetonitrile (5.93 g, 34.4 mmol) in 175 ml of tetrahydrofuran is treated with NaH (60% dispersion in mineral oil; 1.65 g, 41.3 mmol). After 1 hour, (S)-(−)-propylene oxide (4 g, 68.9 mmol) is added, and the resulting mixture is allowed to slowly warm to ambient temperature and stir for 3 days. The reaction mixture is quenched with $H_2O$ and extracted with ethyl acetate. The organic layer is dried over $Na_2SO_4$ and concentrated in vacuo. Purification of the crude residue ($SiO_2$; 10% step gradient of 0 to 40% ethyl acetate in hexanes) affords 2.1 g of the alkylated product (26%).

A 0° C. solution of the alkylated product (1.8 g, 7.82 mmol) in 40 ml of $CH_2Cl_2$ and 3.3 ml of triethylamine is treated with methanesulfonyl chloride (1.2 ml, 15.6 mmol). After 1 hour, the reaction mixture is diluted with ethyl acetate (100 ml) and 1M aqueous $Na_2CO_3$ solution (100 ml). The organic layer is washed with brine, dried over $Na_2SO_4$ and concentrated in vacuo. The crude mesylate is dissolved in 40 ml of dimethylformamide, and $NaN_3$ (1.0 g, 15.6 mmol) is added. The resulting mixture is heated at 60° C. for 4.5 hours, then poured into $H_2O$ (100 ml) and extracted with ethyl acetate (2×100 ml). The combined organic extracts are washed with brine (100 ml), dried over $Na_2SO_4$ and concentrated in vacuo. The crude azide is dissolved in 25 ml of tetrahydrofuran and treated with triphenylphosphine (2.56 g, 9.78 mmol). After stirring at room temperature for 1 hour, the reaction mixture is heated at 60° C. for 3 hours. Water (10 ml) is added to hydrolyze the intermediate aza-ylide and heating is continued for an additional 3 hours. Upon cooling to ambient temperature, the reaction mixture is diluted with ethyl acetate (200 ml) and brine (200 ml). The organic layer is washed with brine (100 ml), dried over $Na_2SO_4$ and concentrated in vacuo. Purification of the crude residue ($SiO_2$; 100% $CHCl_3$ then 2.5% 2M $NH_3$/methanol in $CHCl_3$) affords 1.65 g (7.2 mmol; 92%) of the title amine.

Amines 40 and 41

The title Amines are prepared from methyl indole-4-carboxylate and methyl indole-5-carboxylate, respectively, substantially as described for Amine 39.

Amine 46

A 0° C. solution of indole (7 g, 59.8 mmol) in 200 ml of dimethylformamide is treated with NaH (60% dispersion in mineral oil; 3.1 g, 77.7 mmol). After 20 minutes, bromoacetonitrile (4.2 ml, 59.8 mmol) is added, and the resulting mixture is allowed to slowly warm to ambient temperature and stir overnight. The reaction mixture is diluted with ethyl acetate (500 ml) and washed with $H_2O$ (3×200 ml). The organic layer is dried over $Na_2SO_4$ and concentrated in vacuo. The crude residue is purified by flash chromatography ($SiO_2$; 5% then 20% ethyl acetate in hexanes) to give 2.53 g of indol-1-yl-acetonitrile (27%).

A solution of indol-1-yl-acetonitrile (2.5 g, 16 mmol) in 100 ml of ethanol and 15 ml of anhydrous $NH_3$ is treated with Raney nickel (300 mg). The resulting mixture is heated for 8 hours (80° C.) under an atmosphere of $H_2$ (300 psi). The reaction mixture is filtered over celite and concentrated in vacuo. Purification of the crude residue ($SiO_2$; 2% then 4% 2M $NH_3$/methanol in $CHCl_3$) affords 715 mg of the title amine (28%).

Amines 42, 43, 44 and 48

The title amines are prepared from 5-hydroxyindole, 4-hydroxy-2-methylindole, indole and 6-hydroxyindole, respectively, substantially as described for Amine 39.

Amine 49

A slurry of 4-fluoro-3-(dimethylaminoethyl)-1H-indole (4.3 g, 22.4 mmol) in 14.1 ml of 2-nitropropane is treated with solid NaOH (941 mg, 23.5 mmol), and the resulting mixture is heated at reflux overnight. After cooling to ambient temperature, the reaction mixture is acidified with 10%. aqueous acetic acid (25 ml) and stirring is continued for 30 minutes. The reaction mixture is diluted with ethyl acetate (50 ml) and brine (50 ml). The layers are separated, and the organic layer is washed with brine (50 ml), dried over $Na_2SO_4$ and concentrated in vacuo to give 3.71 g of 4-fluoro-3-(2-methyl-2-nitropropyl)-1H-indole (76%).

A solution of 4-fluoro-3-(2-methyl-2-nitropropyl)-1H-indole (3.7 g, 17.0 mmol) in 95 ml of ethanol and 70 ml of ethyl acetate is treated with 5% Pd/C (900 mg) and the resulting mixture is shaken for 6 hours at ambient temperature under an atmosphere of $H_2$ (60 psi). Additional 5% Pd/C (900 mg) is added, and the reaction mixture is re-subjected to $H_2$ at 60 psi while being heated overnight at 50° C. The reaction mixture is filtered over celite and concentrated in vacuo. Purification of the crude residue ($SiO_2$; 1% step. gradient of 0 to 10% 2M $NH_3$/methanol in $CHCl_3$) affords 1.16 g of the title amine (33%).

Amine 50

Amine 50 is prepared from 5-fluoro-3-(dimethylaminomethyl)-1H-indole in a method similar to that described for the preparation of Amine 49.

Amine 51

Methyl indole-4-carboxylate (7.0 g, 40 mmol) and Eschenmoser's salt (N,N-dimethylmethyleneammonium iodide; 7.8 g, 42 mmol) are combined in 130 ml of acetic acid. After heating at 65° C. for 2 hours, the reaction mixture is concentrated in vacuo. The resulting solid is triturated with ethyl acetate, filtered and dried in vacuo to give 3-dimethylaminomethyl-1H-indole-4-carboxylic acid methyl ester hydroiodide in quantitative yield.

A 0° C. solution of 3-dimethylaminomethyl-1H-indole-4-carboxylic acid methyl ester hydroiodide (19 g, 52.7 mmol) in 75 ml of methanol and 75 ml of 2-nitropropane is treated with dimethyl sulfate (10 ml, 105.5 mmol) and solid sodium methoxide (6.3 g, 110.6.mmol) sequentially. The resulting mixture is allowed to warm to ambient temperature, and, after stirring overnight, the reaction mixture is diluted with ethyl acetate (300 ml) and saturated aqueous $NH_4Cl$ solution (500 ml). The aqueous layer is extracted with ethyl acetate (200 ml), and the combined organic layers are dried over Na$_2$SO$_4$ and concentrated in vacuo to give 3-(2-methyl-2-nitropropyl)-1H-indole-4-carboxylic acid methyl ester in quantitative yield.

A solution of 3-(2-methyl-2-nitropropyl)-1H-indole-4-carboxylic acid methyl ester (14.8 g, 53.6 mmol) in 70 ml of tetrahydrofuran and 70 ml of ethyl acetate is treated with Raney nickel (3.3 g) and the resulting mixture is heated overnight (60° C.) under an atmosphere of H$_2$ (60 psi). The reaction mixture is filtered over celite and concentrated in vacuo. Purification of the crude residue (SiO$_2$; 2.5% step gradient of 2.5 to 20% 2M NH$_3$/methanol in CHCl$_3$) affords 9.21 g of the title amine (71%).

Amine 53

A solution of Amine 52 (1.0 g, 4.06 mmol) and NH$_4$Cl (800 mg, 15 mmol) in 100 ml of methanol is charged with 5 ml of anhydrous NH$_3$. The resulting mixture is sealed in a bomb and heated at 150° C. for 40 hours. The reaction mixture is cooled and concentrated in vacuo. The crude residue is purified by radial chromatography (SiO$_2$; 10% 2M NH$_3$/methanol in CHCl$_3$) to afford 344 mg of the title amine (37%).

Amine 55

A 0° C. solution of 1,2-diamino-2-methylpropane (650 ml, 6.21 mmol), indole-3-carboxylic acid (1.0 g, 6.21 mmol) and N,N-diisopropylethylamine (2.7 ml, 15.2 mmol) in 30 ml of CH$_2$Cl$_2$ is treated with 1-[3-dimethylamino)propyl]-3-ethylcarbodiimide hydrochloride (1.2 g, 6.21 mmol). The resulting mixture is allowed to warm to ambient temperature and stir overnight. The reaction mixture is washed with H$_2$O, dried over Na$_2$SO$_4$ and concentrated in vacuo. Purification of the crude residue (SiO$_2$; 10% 2M NH$_3$/methanol in CHCl$_3$) affords 752 mg of the title amine (52%).

Amine 57

6-Fluoro-3-(2-methyl-2-nitropropyl)-1H-indole is prepared from 6-fluoro-3-(dimethylaminomethyl)-1H-indole by a method similar to that described for Amine 49, paragraph 1.

A solution of 6-fluoro-3-(2-methyl-2-nitropropyl)-1H-indole (1.16 g, 4.91 mmol) in 6 ml of tetrahydrofuran and 12 ml of methanol is treated with CuSO$_4$.5H$_2$O (400 mg, 1.35 mmol) and NaBH$_4$ (882 mg, 23.3 mmol). The resulting mixture is stirred at ambient temperature for 30 minutes and then diluted with H$_2$O (20 ml), CH$_2$Cl$_2$ (20 ml) and concentrated NH$_4$OH (5 ml). After 1 hour, the layers are separated, and the organic layer is dried over Na$_2$SO$_4$ and concentrated in vacuo to afford 951 mg of the title amine (94%).

Amine 58

6-Benzyloxyindole-3-carboxaldehyde is converted to 2-(6-benzyloxy-1H-indoyl-3-yl)-1,1-dimethylethylamine by sequentially following the procedures detailed for Amine 61, 1$^{st}$ paragraph, then for Amine 57, 1$^{st}$ and 2$^{nd}$ paragraphs.

A solution of 2-(6-benzyloxy-1H-indoyl-3-yl)-1,1-dimethylethylamine (4.9 g, 16.6 mmol) in 125 ml of CH$_2$Cl$_2$ is treated with t-butyloxycarbonyl anhydride (BOC$_2$O; 4.0 ml, 17.5 mmol). After stirring overnight at ambient temperature, the reaction mixture is diluted with H$_2$O, and the layers are separated. The organic layer is dried over Na$_2$SO$_4$ and concentrated in vacuo. The crude residue is purified by flash chromatography (SiO$_2$; 20% ethyl acetate in hexanes) to give 5.01 g of [2-(6-benzyloxy-1H-indoyl-3-yl)-1,1-dimethylethyl]carbamic acid tert-butyl ester (76%).

A solution of [2-(6-benzyloxy-1H-indoyl-3-yl)-1,1-dimethylethyl]carbamic acid tert-butyl ester (4.62 g, 11.7 mmol) in 300 ml of ethanol is treated with 5% Pd/C (1.0 g), and the resulting mixture is shaken under an atmosphere of H$_2$ at 60 psi overnight at ambient temperature. The reaction mixture is filtered over celite and concentrated in vacuo. The crude phenol is dissolved in 100 ml of dimethylformamide and treated with triton-B (8.5 ml, 17.6 mmol) and bromoacetonitrile (900 microliters, 12.8 mmol). After 1.5 hours, the reaction mixture is diluted with H$_2$O (100 ml), and the aqueous layer is extracted with ethyl acetate (3×100 ml). The combined organic extracts are washed with H$_2$O (2×100 ml), dried over Na$_2$SO$_4$ and concentrated in vacuo. The crude residue is purified by flash chromatography (SiO$_2$; 20% ethyl acetate in hexanes) affording 954 mg of BOC protected amine 58 (24%).

The BOC protected amine is deprotected substantially as described for Amine 6 to give the title amine 58 in 66% yield.

Amine 59

The title amine is prepared from 5-benzyloxy-3-(dimethylaminomethyl)-1H-indole by following the procedures detailed for Amine 57, 1$^{st}$ and 2$^{nd}$ paragraphs, followed by the methods described for Amine 58, 2$^{nd}$–4$^{th}$ paragraphs.

Amine 60

Amine 60 is prepared from 7-fluoroindole by sequentially following the methods described for Amine 51, 1$^{st}$ paragraph; Amine 49, 1$^{st}$ paragraph; and Amine 51, 3$^{rd}$ paragraph.

Amine 61

A solution of methyl 3-formylindole-6-carboxylate (8.0 g, 39.3 mmol) in 270 ml methanol is treated with dimethylamine (40% aqueous; 267 ml, 2.56 mol) at ambient temperature. After 45 minutes, NaBH4 (4.45 g, 118.1 mmol) is added, and the resulting mixture is heated at 55° C. for 3 hours. The reaction mixture is allowed to cool then is diluted with CHCl$_3$ (200 ml) and brine (I 50 ml). The organic layer is washed with brine, dried over Na$_2$SO$_4$ and concentrated in vacuo. The crude residue is purified by flash chromatography (SiO$_2$; 100% ethyl acetate then 20% 2M NH$_3$/methanol in CHCl$_3$) to give 9.07 g of 3-dimethylamino-methyl-1H-indole-6-carboxylic acid methyl ester(99%). Amine 61 is prepared from 3-dimethylaminomethyl-1H-indole-6-carboxylic acid methyl ester by essentially following the procedures detailed in Amine 49, 1 paragraph; and Amine 51, 3$^{rd}$ paragraph.

Amines 52, 56, 62, 65 and 87

The title amines are prepared from methyl indole-5-carboxylate, 5-cyanoindole, methyl indole-7-carboxylate, 6-cyanoindole and 4-cyanoindole, respectively, in a method similar to that described for the preparation of Amine 51.

Amine 63

Amine 63 is prepared from Amine 62 in 61% yield by essentially following the procedure described for Amine 53.

Amine 64

The title amine is prepared as described for Amines 8a and 8b, $1^{st}$–$6^{th}$ paragraphs.

Amine 66

A solution of [2-(7-hydroxy-1H-indol-3-yl)-1,1-dimethyl-ethyl]-carbamic acid tert-butyl ester (609 mg, 2.0 mmol) is dissolved in dry dimethylformamide (30 ml) under a nitrogen atmosphere and treated with sodium hydride (84 mg, 2.1 mmol, 60% dispersion in oil) added portion-wise over a 10 minute period. The mixture is cooled in an ice/water bath and methyl-2-chloroacetate (434 mg, 4.0 mmol) is added drop-wise over 20 minutes. The ice bath is removed and the mixture stirred at room temperature for 15 hours. The reaction is then quenched with saturated brine and extracted with ethyl acetate. The ethyl acetate layer is dried and concentrated to give a crude residue, which is purified by silica gel chromatography (gradient elution, chloroform with 1%–10% of 20% methanol in acetonitrile) to give 230 mg of [2-(7-(methoxycarbomethoxy)-1H-indol-3-yl)-1,1-dimethyl-ethyl]-carbamic acid tert-butyl ester (30%).

A solution of methanesulfonamide (106 mg, 1.12 mmol) and trimethyl aluminum (2.0 M in hexanes, 0.56 ml, 1.12 mmol) in dry dichloromethane (5.0 ml) is stirred at room temperature under a nitrogen atmosphere for 20 minutes. A solution of [2-(7-(methoxycarbomethoxy)-1H-indol-3-yl)-1,1-dimethyl-ethyl]-carbamic acid tert-butyl ester (160 mg, 0.425 mmol) in dry dichloromethane (1.5 ml) is added and the mixture is heated under reflux for 15 hours. The mixture is cooled to room temperature and quenched with 1 N HCl solution (3.4 ml) and partitioned between ethyl acetate and water. The organic extracts are dried over anhydrous $Na_2SO_4$, filtered and the solvent evaporated to give 220 mg of [2-(7-(methanesulfonamidylcarbomethoxy)-1H-indol-3-yl)-1,1-dimethyl-ethyl]-carbamic acid tert-butyl ester (90%).

The title amine is prepared from [2-(7-(methanesulfonamidylcarbomethoxy)-1H-indol-3-yl)-1,1-dimethyl-ethyl]-carbamic acid tert-butyl ester as described for the preparation of Amine I (108 mg, 70%).

Amine 67

[2-(7-Cyan6methoxy-1H-indol-3-yl)-1,1-dimethyl-ethyl]-carbamic acid tert-butyl ester (500 mg, 1.46 mmol) is dissolved in borane in tetrahydrofuran (3.0 ml of a 1M solution, 3.0 mmol) under a nitrogen atmosphere and the resulting mixture is stirred at room temperature for 18 hours. The mixture is then hydrolyzed by the addition of methanol saturated with HCl gas (1.5 ml) followed by stirring at room temperature for 30 minutes. The solvent is evaporated and the residue treated with saturated aqueous sodium bicarbonate (20 ml). The aqueous mixture is extracted with ethyl acetate (3×25ml). The combined ethyl acetate layers are dried and concentrated to give a crude residue, which is purified by elution from SCX resin (20% of 2M $NH_3$ in methanol in $CHCl_3$) to give after evaporation 390 mg of [2-(7-(2-aminoethoxy)-1H-indol-3-yl)-1,1-dimethyl-ethyl]-carbamic acid tert-butyl ester (77%).

[2-(7-(2-Aminoethoxy)-1H-indol-3-yl)-1,1-dimethyl-ethyl]-carbamic acid tert-butyl ester (270 mg, 0.78 mmol) and 1H-benzotriazol-1-yl methanesulfonate (*Tet. Lett.*, 40:117–120, 1999; 170 mg, 0.82 mmol) in dry dimethylformamide (6.0 ml) is stirred at room temperature under a nitrogen atmosphere for 3 hours. The mixture is diluted with water (20 ml) and extracted with ethyl acetate (2×20 ml). The combined organic extracts are washed with brine, dried over anhydrous $Na_2SO_4$, filtered and the solvent evaporated. The residue is taken up in 5% 2M $NH_3$ in methanol in $CHCl_3$ (5 ml) and the solid removed by filtration. Evaporation of the filtrate gives 270 mg of 2-(7-(2-methanesulfonylaminoethoxy)-1H-indol-3-yl)-1,1-dimethyl-ethyl]-carbamic acid tert-butyl ester (82%).

2-(7-(2-methanesulfonylaminoethoxy)-1H-indol-3-yl)-1,1-dimethyl-ethyl]-carbamic acid tert-butyl ester (350 mg, 0.82 mmol) is deprotected with 4.0M HCl in dioxane to give 170 mg of the tiile compound (89%).

Amines 68–71

The title amines are prepared from trifluoro-methanesulfonic acid 3-(2-tert-butoxycarbonylamino-2-methyl-propyl)-1H-indol-7-yl ester and: 4-methoxycarbonylbenzeneboronic acid; 4-acetamidylbenzeneboronic acid; 3-methoxycarbonylbenzeboronic acid; and 5-methoxycaronylthiophen-2-ylboronic acid, respectively, using the procedure described for the preparation of Amine 2.

Amine 72

The title amine is prepared from [1,1-dimethyl-2-(7-trifluoromethanesulfonylmethyl-1H-indol-3-yl)-ethyl]-carbamic acid tert-butyl ester and 1-vinylimidazole as described for the preparation of Amine 23.(36%) FDMS m/e=282.2 ($M^+$+1).

Amine 73

(2-{7-[2-(4-Cyano-phenyl)-vinyl]-1H-indol-3-yl}-1,1-dimethyl-ethyl)-carbamic acid tert-butyl ester is prepared from [1,1-dimethyl-2-(7-trifluoromethanesulfonylmethyl-1H-indol-3-yl)-ethyl]-carbamic acid tert-butyl ester and 4-cyanostyrene as described for the preparation of Amine 23 (93%). FDMS m/e=315.2 ($M^+$+1).

The title amine is prepared from (2-{7-[2-(4-cyano-phenyl)-vinyl]-1H-indol-3-yl}-1,1-dimethyl-ethyl)-carbamic acid tert-butyl ester as described for the preparation of Amine 28. FDMS m/e=318.2 ($M^+$+1).

Amine 74

{1,1-Dimethyl-2-[7-(2-pyrazin-2-yl-vinyl)-1H-indol-3-yl]-ethyl}-carbamic acid tert-butyl ester is prepared from [1,1-dimethyl-2-(7-trifluoromethanesulfonylmethyl-1H-indol-3-yl)-ethyl]-carbamic acid tert-butyl ester and 2-vinylpyrazine as described for the preparation of Amine 23 (99%). FDMS m/e=393.2 ($M^+$+1)

The Boc-protecting group on {1,1-dimethyl-2-[7-(2-pyrazin-2-yl-vinyl)-1H-indol-3-yl]-ethyl}-carbamic acid tert-butyl ester is removed as described in Amine 6 to give the title amine (94%) FDMS m/e=293.2 ($M^+$+1).

Amine 75

The title amine is prepared from [1,1-dimethyl-2-(7-trifluoromethanesulfonylmethyl-1H-indol-3-yl)-ethyl]-carbamic acid tert-butyl ester and p-sulfonamido styrene as described for the preparation of Amine 23 (70%). FDMS m/e=370.2 (M$^+$+1).

Amine 76

Trifluoro-methanesulfonic acid 3-(2-tert-butoxycarbonylamino-2-methyl-propyl)-1H-indol-6-yl ester is prepared from 6-benzyloxy gramine and 2-nitropropane as described in the preparation of Amine 1, 1$^{st}$–5$^{th}$ paragraphs. Trifluoromethanesulfonic acid 3-(2-tert-butoxycarbonylamino-2-methyl-propyl)-1H-indol-6-yl ester and acrylonitrile are reacted and the Boc-protecting group is removed from the resulting product as described in the preparation of Amine 23 to give the title amine (75%). FDMS m/e=240.2 (M$^+$+1).

Amine 77

The 7-nitroindole (20.0 g, 123.3 mmol) and Eschenmoser's salt (24.0 g, 129.5 mmol) are suspended in glacial acetic acid (500 mL) and stirred at 65° C. for 1 hour. The reaction mixture is cooled and the resulting solid filtered, and washed with ethyl acetate (2×50 mL). This solid is then dried in a vacuum oven overnight to yield 39.3 g of the desired 7-nitrogramine hydroiodide salt (89.4%).

The 7-nitrogramine salt (2.0 g, 5.8 mmol) is suspended in a mixture of 2-nitropropane (9.5 mL) and methanol (9.5 mL). Dimethylsulfate (1.09 mL, 11.5 mmol) is added dropwise via syringe, and the resulting yellow solution is stirred at room temperature for 5 minutes. Sodium methoxide (0.62 g, 11.5 mmol) is then added in one portion, and the mixture is stirred overnight at room temperature. The reaction is quenched by addition of saturated NH$_4$Cl solution and ethyl acetate. The aqueous layer is extracted with ethyl acetate, and the combined organic layers are washed with brine, and dried over Na$_2$SO$_4$ to give 1.0 g of 3-(2-nitro-2-methylpropyl)-7-nitroindole (69%).

3-(2-Nitro-2-methylpropyl)-7-nitroindole (1.89 g, 7.2 mmol) is dissolved in ethyl acetate (75 mL) and 10% Pd/C is added (750 mg). The mixture is stirred under a balloon of nitrogen for 2–3 hours. The mixture is filtered to remove the Pd/C, and the filtrate is evaporated to give a crude oil. This crude 3-(2-nitro-2-methylpropyl)-7-aminoindole is immediately dissolved in pyridine (100 mL) and the solution is cooled with an ice bath to 0° C. Benzenesulfonyl chloride is added slowly, and the mixture is stirred for 5 minutes at this temperature before removing the ice bath. The reaction mixture is stirred overnight before being quenched by addition of IN HCl and ethyl acetate. The aqueous layer is extracted with ethyl acetate several times and the combined organic extracts are washed twice with brine and dried over Na$_2$SO$_4$ to give a crude oil. The crude material is purified by flash chromatography (25% ethyl acetate/hexanes) to provide 1.9 g of 3-(2-nitro-2-methylpropyl)-7-benzenesulfonamidyl-indole (71%).

3-(2-Nitro-2-methylpropyl)-7-benzenesulfonamidyl-indole, (1.90 g, 5.1 mmol) is charged to a Parr reaction vessel and is dissolved in 3A-ethanol (500 mL). Raney Nickel (5 g) is added to the solution. The reaction is pressurized with hydrogen and is hydrogenated overnight at 60° C. under a hydrogen pressure of 60 psi. When the reaction is complete, the reaction mixture is cooled to ambient temperature and the Raney Nickel is removed by vacuum filtration. The solvent is evaporated to give the title amine.

Amine 78

3-(2-Nitro-2-methylpropyl)-7-methanesulfonamidyl-indole is prepared from crude 3-(2-nitro-2-methylpropyl)-7-aminoindole and methanesulfonyl chloride and 3-(2-nitro-2-methylpropyl)-7-methanesulfonamidyl-indole is converted to the title amine by the procedure described for Amine 77 (2.3 g).

Amine 79

The Boc-protected title amine is prepared from Boc-α-methylalanine and indoline by the procedure described above for Amine 20 except that the reaction is conducted in dichloromethane and the crude Boc-protected amine is purified by normal phase flash chromatography (silica gel, 20–60% ethyl acetate/hexanes).

To a mixture of the Boc-protected title amine (1.0 g, 3.3 mmol) in dioxane (8 mL) at room temperature is added 4M HCl/dioxane (8 mL). The reaction mixture is stirred overnight at room temperature, and then concentrated. The resulting material is dissolved in methanol (10 mL), purified using a cation exchange column, and concentrated to give 640 mg of the title amine (95%).

Amine 80

To a solution of {1,1-dimethyl-2-[7-(2-[1,2,4]triazol-1-yl-vinyl)-1H-indol-3-yl]-ethyl}-carbamic acid tert-butyl ester (1.0 g, 2.55 mmol) in methanol (20.0 mL), is added 10% Pd/C (0.50 g) in methanol (2.0 mL). The reaction mixture is purged with hydrogen and hydrogenation is carried out with a hydrogen balloon overnight. The reaction mixture is filtered, and the filtrate is evaporated to dryness to give 850 mg of {2-[7-(2-methanesulfonyl-ethyl)-1H-indol-3-yl]-1,1-dimethyl-ethyl}-carbamic acid tert-butyl ester (81%). FDMS m/e=395.2 (M$^+$+1).

To solution of {1,1-Dimethyl-2-[7-(2-[1,2,4]triazol-1-yl-ethyl)-1H-indol-3-yl]-ethyl}-carbamic acid tert-butyl ester (220 mg, 0.57 mmol) in dioxane (5.0 mL) at room temperature is added 4N HCl (5.0 mL). The reaction mixture is stirred at room temperature for 1 hour. The reaction mixture is evaporated to dryness, residue is taken up with water (25.0 mL), saturated NaHCO$_3$ (5.0.mL) is added, and the mixture is extracted with ethyl acetate (2×50 mL). The organic extracts are washed with brine, dried (Na$_2$SO$_4$) and evaporated to dryness to give 150 mg of the title amine (90%).

Amine 81

3-Trifluoromethyl-bromobenzene (I equivalent) is dissolved in dimethylsulfoxide (3 ml/mmol) under argon and bis-(pinacolato)-diboron (1.1 equivalents), potassium acetate (3 equivalents) and 1,1'-bis(diphenylphosphino)ferrocene)palladium(II)dichloride-dichlormethane complex (0.03 equivalents) are added. The resulting mixture is heated to 80° C. and then stirred for two hours at this temperature. The mixture is cooled to room temperature, and trifluoromethansulfonic acid 3-(2-tert-butoxycarbonylamino-2-methyl-propyl)-1H-indol-7-yl ester (0.8 equivalents), 1,1'-bis (diphenylphosphino) ferrocene)palladium(II)dichloride-dichlormethane (0.03 equivalents) and 2M Na$_2$CO$_3$ (5 equivalents) are added under argon. The resulting mixture is heated to 80° C. and then allowed to stir overnight at this temperature. The mixture is diluted with water and extracted with ethyl acetate or $CH_2Cl_2$. The organic extract is washed once with brine, then dried over $Na_2SO_4$, filtered and evaporated. The residue is chromatographed (silica gel, $CH_2Cl_2$/ethanolic $NH_3$, 98/2) to give the Boc-protected title compound.

The Boc-protected amine is dissolved in 5N HCl in isopropanol (5 ml/mmol) and stirred overnight at room temperature. The mixture is evaporated, dissolved in ethanol and loaded onto a 5 g SCX column conditioned with methanol. The column is washed twice with 5 ml ethanol to remove impurities. The title compound is then eluted with 5 ml ethanolic $NH_3$ and 5 ml ethanol. Evaporation of the solvent gives the deprotected amine.

Amines 82–84

The title amines are prepared from trifluoro-methansulfonic acid 3-(2-tert-butoxycarbonylamino-2-methyl-propyl)-1H-indol-7-yl ester and: ethyl 3-bromobenzoate; 3'-bromoacetophenone; and 4'-bromoacetophenone, respectively, using the procedure described for the preparation of Amine 81.

Amine 85

Amine 85 is prepared by hydrolysis of the methyl ester of Amine 62 by essentially following the procedure detailed for Amine 86.

Amine 86

A solution Amine 61(2 g, 8.12 mmol) in 24 ml of tetrahydrofuran and 8 ml of MeOH is treated with 1M aqueous LiOH (8.1 ml). The resulting mixture is heated overnight at 60° C. An additional portion of 1M aqueous LiOH (2 ml) is added and heating is continued for 24 hours to drive the hydrolysis to completion. The reaction mixture is concentrated in vacuo to give the crude lithium salt as a white solid.

Amine 88

Amine 88 is prepared from indole-2-carboxylic acid and 1,2-diamino-2-methylpropane by essentially following the procedure detailed for Amine 55.

EXAMPLES

Representative Procedure 1: Amination of Epoxide

A vial is charged with a solution of single amine of formula III (0.2M in ethanol or t-butanol, 90 micromolar) and a solution of a single epoxide of formula II (0.2M in dimethylsulfoxide, 80 micromolar). The vial is sealed and heated to 80° C. for 24–48 hours. The solution is cooled to room temperature, diluted with methanol, and passed over a cation exchange column, eluting the basic material with 1N methanolic ammonia.

Representative Procedure 2: Amination of Epoxide

A stirred mixture of an epoxide of formula II (1 equivalent) and an amine of formula III (1–2 equivalents) in ethanol, methanol, n-butanol or t-butanol is heated at 70–80° C. for 2–72 hours. The solvent is evaporated to dryness to give a crude oil that is optionally diluted with methanol or ethanol and passed over a cation exchange column (eluting the free base product with 1N methanolic ammonia) before further purification.

The final products prepared via Representative Procedure 1 or 2 may be further purified by flash or radial chromatography. Typical chromatography conditions include: a) using a variable mixture of 25:5:1 chloroform/methanol/ammonium hydroxide and 9:1 chloroform/methanol; b) a variable mixture of 90:10:1 $CH_2Cl2$/ethanolic $NH_3$ gradient; c) dichloromethane/6–12% methanol, 0.15–0.35M ammonia in dichloromethane gradient; d) methylene chloride with a step gradient to 2–8% methanol; e) chloroform/2.0M ammonia in methanol, from 0–10% to 6–20% gradient elution or f) isocratic 6–8% 2M ammonia in methanol: 92–94% dichloromethane.

Alternatively, the final products may be purified on C18 bonded silica gel using either mass guided or UV guided reverse phase liquid chromatography (acetonitrile/water with 0.01% hydrochloric acid or 0.1% trifluoroacetic acid). When purification of a compound of the present invention results in production of a free base, the free base thus prepared may be salified, e.g., by dissolution of the free base in $CH_2Cl_2$ or diethylether, adding 1M ethanolic HCl or a solution of HCl in diethylether, and evaporating the volatiles, or as described in more detail below.

For example, a hydrochloride salt may be prepared by dissolving the free base in dichloromethane, diethylether, or a mixture of ethyl acetate and methanol and adding 1M ethanolic HCl, a solution of HCl in diethylether, or 0.5M ammonium chloride. The resulting mixture is allowed to stir for a short time, e.g., for five minutes, before evaporating the volatiles and optionally triturating in diethyl ether to give the hydrochloride salt.

The oxalate salts may be prepared by dissolving the free base in a small amount of ethyl acetate, optionally adding methanol for solubility. The resulting solution is treated with 1 equivalent of a 0.5M solution of oxalic acid in ethyl acetate. The reaction mixture is either concentrated in vacuo or centrifuged, separated, and the solids are dried, to give the oxalate salt.

To prepare a succinate salt, the free base may be dissolved in a small amount of ethyl acetate or methanol and then treated with 1 equivalent of succinic acid in methanol. The resulting slurry is dissolved in the minimum amount of methanol then concentrated in vacuo to give the succinate salt.

The table below sets out representative combinations of Amines and Epoxides that are reacted as described in Representative Procedure 1 or 2. Preparation of desired product is confirmed via mass spectral analysis (MSA). Emax ± Standard Error Mean (SEM) data, discussed in the "Demonstration of Function" section below, is also included for said compounds where available. The Emax values represent the average of at least 3 runs except as otherwise indicated.

TABLE 3

| E.g. | Epoxide | Amine | MSA | Isolated Form | Emax (%) ± SEM |
|---|---|---|---|---|---|
| 1 | 3 | 2 | 592.0 | Succinate | 58.6 ± 3.3 |
| 2 | 3 | 3 | 530.0 | Succinate | 55.4 ± 5.6 |
| 3 | 3 | 12 | 566.0 | Succinate | 75.1 ± 5.7 |
| 4 | 3 | 14 | 566.0 | Succinate | 65.4 ± 4.8 |
| 5 | 3 | 16 | 500.9 | Oxalate | 35.1 ± 3.3 |
| 6 | 3 | 17 | 465.2 | Oxalate | 69.7 ± 1.5 |
| 7 | 3 | 18 | 449.0 | Hydrochloride | 67.1 ± 2.3 |

TABLE 3-continued

| E.g. | Epoxide | Amine | MSA | Isolated Form | Emax (%) ± SEM |
|---|---|---|---|---|---|
| 8 | 3 | 20 | 450.2 | Free Base | 45.1 ± 5.3 |
| 9 | 3 | 21 | 450.2 | Free Base | 22.2 ± 3.8 |
| 10 | 3 | 19 | 436.3 | Hydrochloride | 58.6 ± 4.7 |
| 11 | 1 | 11 | 422.3 | Hydrochloride | 79.9 ± 2.7 |
| 12 | 2 | 11 | 434.3 | Hydrochloride | 71.0 ± 2.3 |
| 13 | 3 | 6 | 503.5 | Hydrochloride | 73.3 ± 4.7 |
| 14 | 1 | 6 | 477.4 | Hydrochloride | 74.9 ± 3.9 |
| 15 | 2 | 6 | 489.4 | Hydrochloride | 72.6 ± 2.6 |
| 16 | 3 | 31 | 541.2 | Succinate | 49.0 ± 3.0 |
| 17 | 3 | 26 | 519.2 | Succinate | 67.2 ± 1.5 |
| 18 | 3 | 27 | 552.2 | Succinate | 64.1 ± 2.1 |
| 19 | 3 | 28 | 554.2 | Succinate | 65.3 ± 5.2 |
| 20 | 3 | 30 | 501.2 | Succinate | 67.5 ± 4.6 |
| 21 | 3 | 39 | 489.1 | Oxalate | 50.9 ± 4.4 |
| 22 | 3 | 11 | 448.3 | Hydrochloride | 66.1 ± 4.5 |
| 23 | 3 | 44 | 434.2 | Hydrochloride | 56.8 ± 0.7 |
| 24 | 3 | 51 | 506.3 | Hydrochloride | 38.5 ± 2.0 |
| 25 | 3 | 52 | 506.3 | Hydrochloride | 38.3 ± 3.2 |
| 26 | 3 | 49 | 466.3 | Hydrochloride | 65.4 ± 2.2 |
| 27 | 3 | 50 | 466.3 | Hydrochloride | 58.6 ± 0.9 |
| 28 | 3 | 53 | 491.1 | Hydrochloride | 44.4 ± 5.6 |
| 29 | 3 | 54 | 448.3 | Hydrochloride | 58.0 ± 1.6 |
| 30 | 3 | 55 | 491.1 | Hydrochloride | 39.0 ± 2.3 |
| 31 | 3 | 56 | 473.2 | Hydrochloride | 35.2 ± 3.6 |
| 32 | 3 | 61 | 506.3 | Hydrochloride | 48.5 ± 5.6 |
| 33 | 3 | 61 | 506.3 | Hydrochloride | 51.6 ± 2.4 |
| 34 | 3 | 57 | 466.3 | Hydrochloride | 65.3 ± 1.6 |
| 35 | 3 | 16 | 466.3 | Hydrochloride | 61.6 ± 0.7 |
| 36 | 3 | 17 | 490.6 | Hydrochloride | 54.5 ± 0.5 |
| 37 | 3 | 65 | 473.3 | Hydrochloride | 61.4 ± 1.4 |
| 38 | 3 | 66 | 599.0 | Free Base | 80.4 ± 2.0 |
| 39 | 3 | 32 | 488.3 | Free Base | 40.2 ± 1.3 |
| 40 | 3 | 67 | 585.0 | Free Base | 79.6 ± 1.0 |
| 41 | 3 | 5 | 660.0 | Succinate | 76.5 ± 2.2 |
| 42 | 3 | 68 | 582.0 | Succinate | 59.1 ± 3.2 |
| 43 | 3 | 69 | 581.0 | Succinate | 73.4 ± 1.8 |
| 44 | 3 | 70 | 582.0 | Succinate | Not Tested |
| 45 | 3 | 71 | 588.0 | Free Base | Not Tested |
| 46 | 3 | 77 | 603.2 | Hydrochloride | 79.4 ± 4.6 |
| 47 | 3 | 78 | 541.2 | Hydrochloride | 69.7 ± 2.4 |
| 48 | 2 | 28 | 539.3 | Succinate | 74.3 ± 7.0 |
| 49 | 3 | 74 | 552.2 | Succinate | 68.5 ± 2.4 |
| 50 | 3 | 75 | 629.2 | Free Base | 77.3 ± 1.9 |
| 51 | 3 | 80 | 543.2 | Succinate | 70.0 ± 1.2 |
| 52 | 2 | 80 | 529.3 | Succinate | 73.6 ± 5.1 |
| 53 | 3 | 81 | 592.2 | Hydrochloride | 57.3 ± 5.0 |
| 54 | 3 | 82 | 596.4 | Hydrochloride | 68.9 ± 5.9 |
| 55 | 3 | 68 | 582.2 | Hydrochloride | 69.9 ± 3.0 |
| 56 | 3 | 83 | 566.4 | Hydrochloride | 64.5 ± 2.4 |
| 57 | 3 | 84 | 566.4 | Hydrochloride | 63.1 ± 2.7 |
| 58 | 3 | 78 | 541.2 | Hydrochloride | 69.7 ± 2.4 |
| 59 | 1 | 17 | 439.3 | Hydrochloride | 72.0 ± 5.9 |
| 60 | 2 | 17 | 451.3 | Hydrochloride | 69.2 ± 6.5 |
| 61 | 2 | 85 | 478.2 | Hydrochloride | 72.1 ± 1.4 |
| 62 | 2 | 86 | 478.2 | Hydrochloride | 69.5 ± 6.6 |
| 63 | 3 | 79 | 464.3 | Hydrochloride | 44.2 ± 5.1 |
| 64 | 3 | 87 | 473.3 | Hydrochloride | 51.1 ± 3.1 |
| 65 | 3 | 24 | 534.1 | Free Base | Not Tested |

EXAMPLE 66

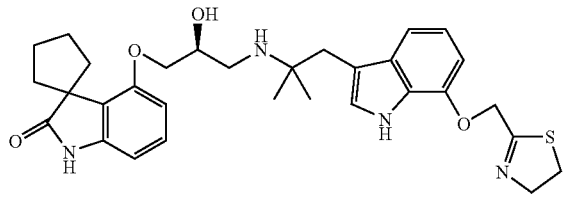

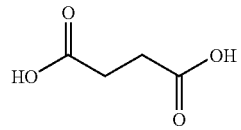

To a solution of the compound of Example 13 (1 equivalent) in ethanol (0.02 mol solute/mL), is added cysteamine (1.2 equivalents). The resulting mixture is reluxed overnight. The reaction mixture is cooled to room temperature and evaporated to dryness. The resulting residue is chromatographed (5% 2N methanolic ammonia in dichloromathane) to give the free base of the title compound. Succinic acid (1 equivalent) in methanol is added to the free base, the mixture is allowed to stir then is evaporated to dryness to give the title compound. FDMS m/e=501.2 ($M^+$+1). Emax (SEM)=84.9 (2.8).

EXAMPLE 67

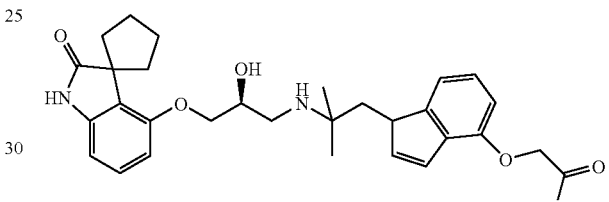

Amine 6 is alkylated with Epoxide 3 in t-butanol in a manner similar to that described Representative Procedure 2 to give the coupled product. The solution of the crude intermediate nitrile (0.185 mmol) in 1.5 ml of t-butanol is then treated directly with NaOH (100 mg). Ethanol (1.5 ml) is added to aid solubility, and the resulting mixture is heated at 80° C. for 6 hours. The reaction mixture is concentrated in vacuo and purified by reverse phase HPLC (YMC ODSA C18 5micrometer column, gradient of 5–95% $CH_3CN$ in $H_2O$ with 0.01% HCl, 20 ml/minute, over 12 minutes) to give 21.6 mg of the title compound (21%). MS 522.3. Emax (SEM)=80.1(6.2).

EXAMPLE 68

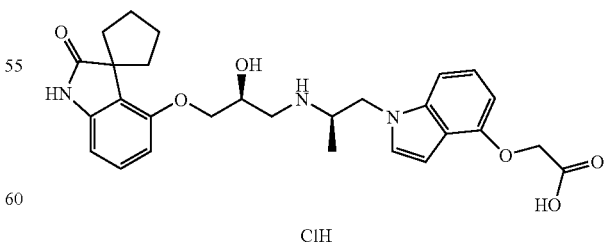

The title compound is prepared by hydrolysis of the compound of Example 21 with NaOH in a manner similar to that described in Example 67. MS: 508.1. Emax (SEM) =73.3 (1.2).

EXAMPLE 69

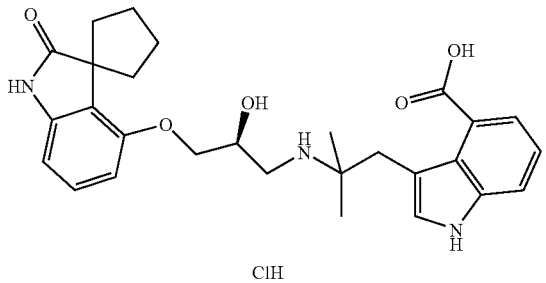

ClH

A solution of the free base of the compound of Example 24 (196 mg, 0.388 mmol) in 1.2 ml of 3:1:1 tetrahydrofuran:methanol:H$_2$O is treated with LiOH (30 mg, 1.25 mmol). The resulting mixture is heated overnight at 60° C. then concentrated in vacuo. Purification of the crude product by reverse phase HPLC (YMC ODSA C18 5micrometer column, gradient of 5–95% CH$_3$CN in H$_2$O with 0.1% HCl, 20 ml/minute, over 12 minutes) affords 115 mg of the title compound (53%). MS 492.4. Emax (SEM)=37.9 (5.0).

EXAMPLE 70

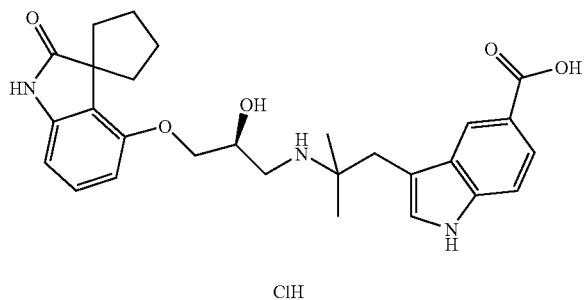

ClH

The title compound is prepared in 19% yield by hydrolysis of the compound of Example 25 in a method similar to that detailed in Example 69. MS 492.4. Emax (SEM)=53.5 (2.4).

EXAMPLE 71

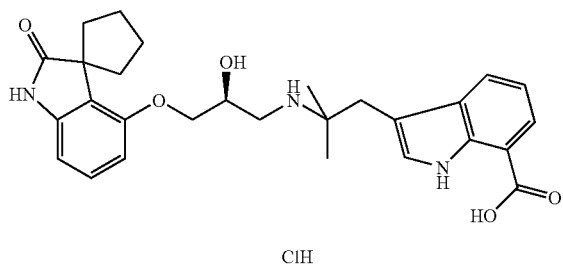

ClH

The title compound is prepared by hydrolysis of the compound of Example 33 in a method similar to that detailed in Example 69. MS 492.2. Emax (SEM)=59.5 (4.9).

EXAMPLE 72

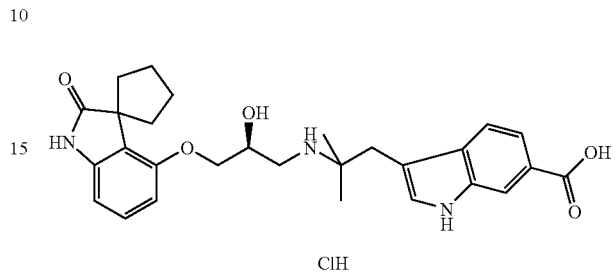

ClH

The title compound is prepared by hydrolysis of the compound of Example 32 in a method similar to that detailed in Example 69. 492.3. Emax (SEM)=56.2 (4.3).

EXAMPLE 73

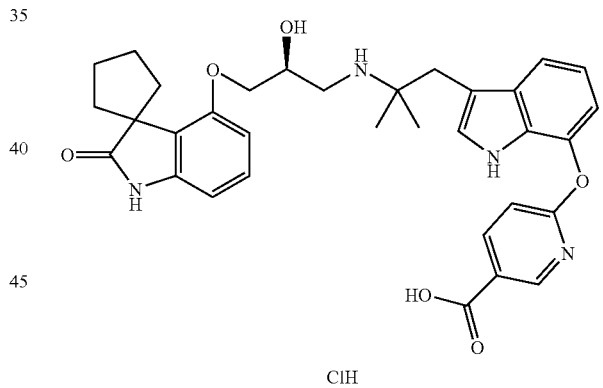

ClH

The compound of Example 4 (103 mg) is dissolved in methanol. 2N Sodium hydroxide is added and the mixture is refluxed for 1.6 hours. Water is added and the pH of the mixture is adjusted to 3 using 1N hydrochloric acid. The aqueous mixture is extracted with ethyl acetate (3 times). The combined organic extracts are dried with anhydrous sodium sulfate, filtered, and the solvent is evaporated. The product is purified using HPLC (5–95% solvent B in 3.8 minutes on YMC ODS-A (0.46×50mm), solvent A=0.1% trifluoroacetic acid/water, solvent B=0:1% trifluoroacetic acid/acetonitrile) to give 12.5 mg of the title compound. FDMS m/e=585 (M$^+$+1 of free base). Emax (SEM)=82.4 (5.4).

EXAMPLE 74

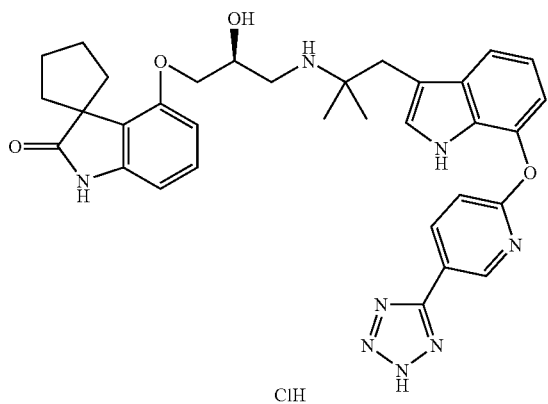

The compound of Example 4.(1 01 mg, 1.0 eq), azidotrimethylsilane (206 mg, 10.0 eq), and dimethyltin oxide (15 mg, 0.5 eq) are dissolved in toluene and mixture is refluxed for 16 hours. The solvent is evaporated and the residue is dissolved in methanol. The solution is passed through a plug of silica gel to trap the tin compound. The filtrate is evaporated and the compound purified by HPLC (5–95% solvent B in 3.8 minutes on YMC ODS-A (0.46×50mm), solvent A=0.1% trifluoroacetic acid/water, solvent B=0.1% hydrochloric acid/acetonitrile) to give 66.8 mg of title compound. FDMS m/e=609 (M$^+$+1 of free base). Emax (SEM) =78.1(5.9).

EXAMPLE 75

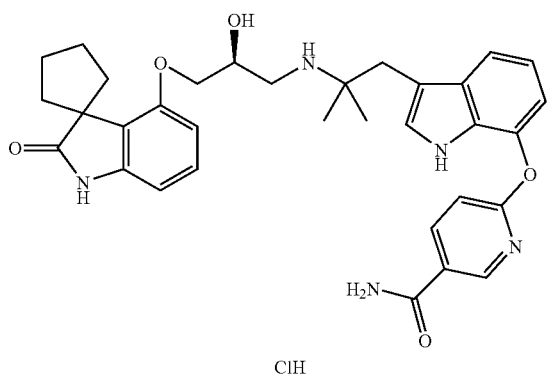

Potassium carbonate is added to dimethylsulfoxide. The mixture is stirred under nitrogen, and heated to 50° C. for 30 minutes. The mixture is cooled to room temperature, and the compound of Example 4 dissolved in dimethylsulfoxide is added to the mixture, followed by the addition of water dropwise. The mixture is allowed to stir for 10 to 15 minutes, then 30% hydrogen peroxide is added dropwise. After 20 minutes, saturated aqueous sodium sulfite solution and water is added and the mixture is extracted 3 times with of ethyl acetate. The combined organic layers and dried with sodium sulfate, filtered and evaporated to give the free base of the title compound. The product is purified using HPLC (5–95% solvent B in 3.8 minutes on YMC ODS-A (0.46× 50mm), solvent A=0.1% trifluoroacetic acid/water, solvent B=0.1% hydrochloric acid/acetonitrile) to give 52.3 mg of the title compound. FDMS m/e=584 (M$^+$+1 of free base). Emax (SEM)=80.1 (5.6).

EXAMPLE 76

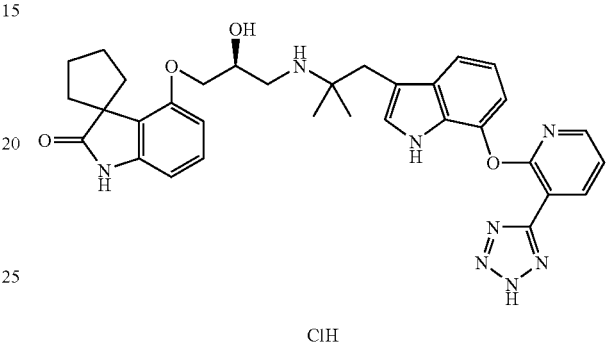

Crude title compound is prepared from the compound of Example 3 (96 mg) via the procedure described in Example 74. The product is purified using HPLC (5–95% solvent B in 3.8 minutes on YMC ODS-A (0.46×50mm), solvent A=0.1% hydrochloric acid/water, solvent B=0.1% trifluoroacetic acid/acetonitrile) to give 36.6 mg of title compound. FDMS m/e=609 (M$^+$+1 of free base). Emax (SEM)=80.1 (4.0).

EXAMPLE 77

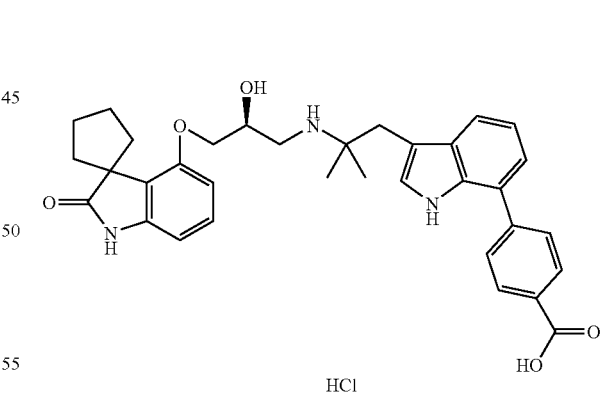

To a solution of the compound of Example 42 (1 equivalent) in methanol is added sodium hydroxide (0.93 mL, 2M, 1.86 mmol). The mixture is refluxed for 4 hours then diluted with HCl and extracted three times with ethyl acetate. The combined extracts are dried over sodium sulfate, filtered and evaporated. The residue is chromatographed by reverse phase HPLC (acetonitrile/0.01% HCl in water) to give the title compound. FDMS m/e=568 (M$^+$+1 of free base). Emax (SEM)=79.9-(6.8).

EXAMPLE 78

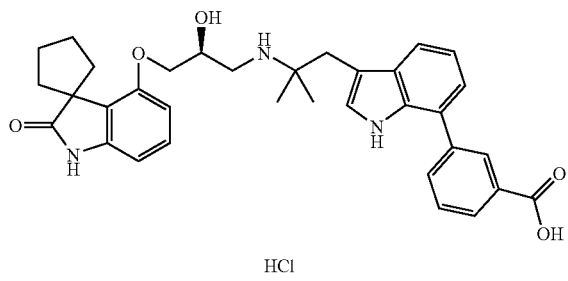

HCl

The compound of Example 44 is converted to the title compound via the procedure described for the preparation of Example 77 (58%). FDMS m/e=568 (M$^+$+1 of free base). Emax (SEM)=93.5 (10.4).

EXAMPLE 79

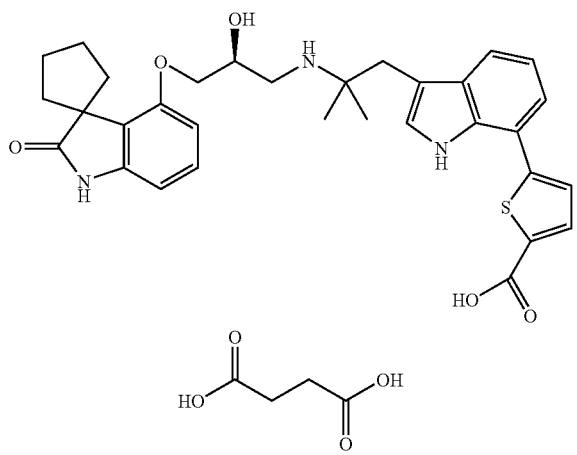

The compound of Example 45 is converted to the free base of the title compound via the procedure described for the preparation of Example 77 except that chromatography on the crude free base is not performed. Instead, the crude free base is dissolved in a small amount of ethyl acetate and treated with 1 equivalent of succinic acid in methanol. The resulting slurry is dissolved in the minimum amount of methanol then concentrated in vacuo to give the title compound (61%). FDMS m/e=574 (M$^+$+1 of free base). Emax (SEM)=75.1(3.8).

EXAMPLE 80

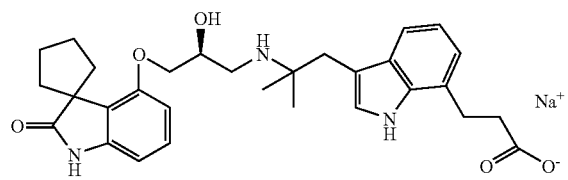

The compound of Example 65 (80 mg, 0.15 mmole) is dissolved in methanol (10.0 mL). 2N NaOH (0.5 mL) is added and the reaction mixture is heated to reflux for 1.5 hours. The mixture is cooled to room temperature, evaporated to about 2 mL, then diluted to 20 mL with water. The reaction mixture is evaporated to about 2 mL then diluted to 20 mL with water. The resulting solution is passed through a C18 Cartridge, washed with water (50 mL) and eluted with methanol (25 mL). The methanol eluent is evaporated to give the title compound (90%). FDMS m/e=520.2 (M$^+$+1). Emax (SEM)=77.2 (3.5).

EXAMPLE 81

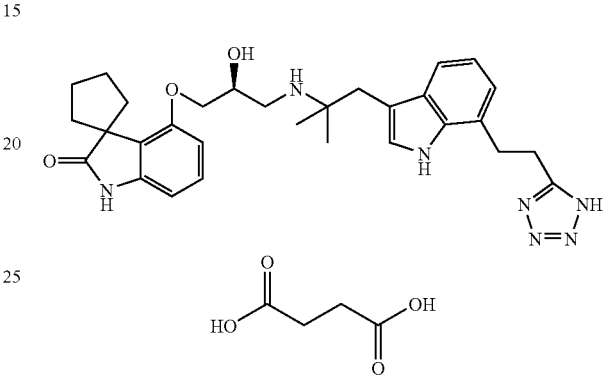

To a solution of the free base of the compound of Example 20 (2 equivalents) in toluene is added dimethyltin oxide (1 equivalent) and azidotrimethylsilane (20 equivalents). The reaction mixture is heated to reflux overnight. The reaction mixture is cooled to room temperature and evaporated to dryness. The resulting residue is chromatographed with 20% methanol (2N ammonia) in dichloromethane to give the free base of the title compound. Succinic acid (1 equivalent) in methanol is added to the free base and the resulting mixture is allowed to stir before evaporating to dryness to give the title compound. FDMS m/e=544.0 (M$^+$+1). Emax (SEM)=77.4 (3.3).

EXAMPLE 82

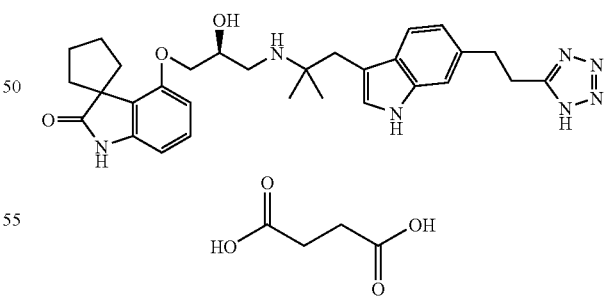

Epoxide 3 and Amine 76 are reacted and the resulting ethanolamine free base product is isolated as described above in Representative Procedure 2. This free base is reacted with azidotrimethylsilane as described above in Example 81 to give the 6-vinyl analogue of the title compound. The vinyl group is hydrogenated as described above for Amine 28 to give the title compound. FDMS m/e=544.2 (M$^+$+1). Emax (SEM)=72.7 (1.8).

EXAMPLE 83

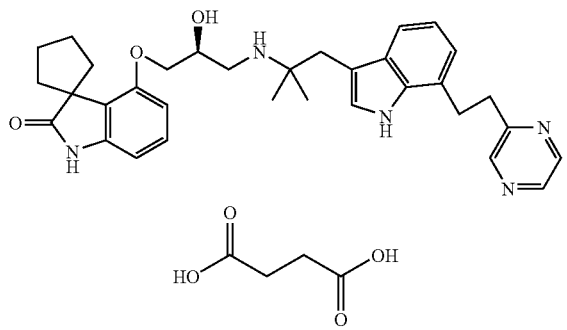

To a solution of the compound of Example 49 (1.02 mmol) in methanol is added 10% Pd/C (100 mg/mmol of substrate) in methanol. The reaction mixture is purged with hydrogen and hydrogenation is carried out with a hydrogen balloon overnight. The reaction mixture is filtered and the filtrate is evaporated to dryness to give the title compound. FDMS m/e=554.2 ($M^+$+1). Emax (SEM)=79.3 (7.8).

EXAMPLE 84

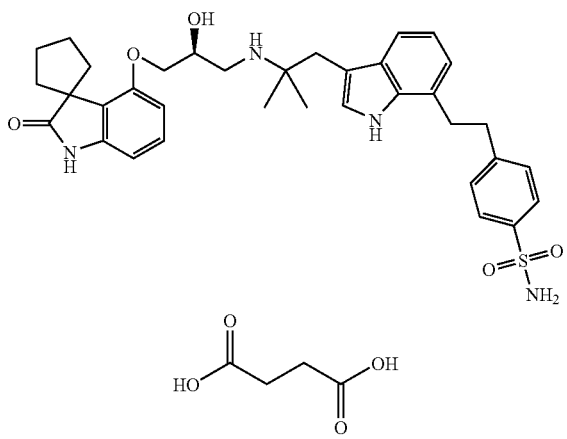

The title compound is prepared from the compound of Example 50 as described for Preparation of Example 83. FDMS m/e=631.3 ($M^+$+1). Emax (SEM)=78.5 (2.9).

EXAMPLE 85

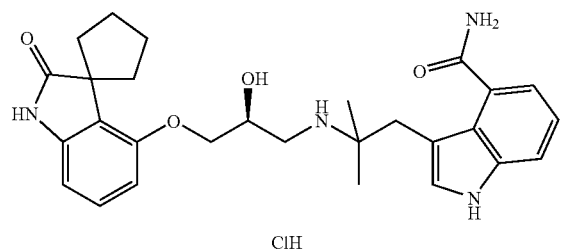

A solution of the crude free base of Example 64 (302 mg, 0.64 mmol) in 7.5 ml of dimethylsulfoxide is treated with powdered $K_2CO_3$ (177 mg, 1.28 mmol). The resulting mixture is cooled to 0° C., and 73 µl of 30% $H_2O_2$ is added dropwise. After stirring overnight, 1 ml of 20% KOH and an additional 200 µl of 30% $H_2O_2$ is added to the reaction mixture. After stirring overnight, 20 ml of $H_2O$ is added, and the resulting mixture is cooled in an ice $H_2O$ bath for 1 hour, then extracted with $CHCl_3$. The organic layer is washed with brine, dried over $Na_2SO_4$ and concentrated in vacuo. The residue is purified by reverse phase HPLC (YMC ODSA C 18 5 µm column, gradient of 5–95% $CH_3CN$ in $H_2O$ with 0.01% HCl, 20 ml/minute, over 12 minutes) to give 45.3 mg of the title compound (13%). MS 491.3. Emax (SEM)=48.3 (4.2).

Demonstration of Function

The genes encoding the human $\beta_1$-adrenergic receptor (Frielle et al., *Proc. Natl. Acad. Sci.*, 84:7920–7924, 1987), the human $\beta_2$-adrenergic receptor (Kobika el al., *Proc. Natl. Acad. Sci.*, 84:46–50, 1987, Emorine et al., *Proc. Natl. Acad. Sci.*, 84:6995–6999, 1987) and the human $\beta_3$ adrenergic receptor (Granneman et al., *Molecular Pharmacology*, 44(2):264–70, 1993) are individually subcloned into a phd expression vector (Grinnell et al., *Bio/Technology*, 5:1189–1192, 1987) and transfected into the DXB-11 Chinese hamster ovary (CHO) cell line by calcium phosphate precipitation methodology. The stably transfected cells are grown to 95% confluency in 95% Dulbecco's modified Eagles Medium (DMEM), 5% fetal bovine serum and 0.01% proline. Media is removed and the cells are washed with phosphate buffered (pH 7.4) saline (without magnesium and calcium). Cells are then lifted using an enzyme free cell dissociation solution (Specialty Media, Lavallette, N.J.) and pelleted by centrifugation.

Cells from each of the above cell lines are resuspended and added (20,000/well) to a 96-well plate. Cells are incubated at 37° C. with representative compounds of the invention for 20 minutes in buffer (Hank's balanced salt solution, 10 mM HEPES, 0.1% BSA, 1 mM L-ascorbic acid, 0.2% dimethyl sulfoxide, 1 mM 3-isobutyl-1-methylxanthine, pH 7.4). After halting the incubation with quench buffer (50 mM Na Acetate, 0.25% Triton X-100, pH 5.8), the c-AMP level is quantified by scintillation proximity assay (SPA) using a modification of the commercially available c-AMP kit (Amersham, Arlington Heights, Ill.) with rabbit anti-cAMP antibody (ICN Biomedicals, Aurora, Ohio) for the kit.

Sigmoidal dose response curves, from the whole cell receptor coupled c-AMP assay are fit to a four parameter logistic equation using non linear regression: $y=(a-d)/(1+(Dose/c)^b)+d$ where a and d are responses at zero and maximal dose, b is the slope factor and c is the $EC_{50}$ as previously described (DeLean et al., *Am. J. Physiol.*, 235, E97–E102, 1978). $EC_{50}$ is assessed as the concentration producing 50% of the maximum response to each agonist.

Isoproterenol is accepted in the art as a non-selective $\beta_3$ agonist and is widely used as a comparator in evaluating the activity of compounds. See *Trends in Pharm. Sci.*, 15:3, 1994. The % intrinsic activity (Emax) of representative compounds of the invention is assessed relative to isoproterenol by the compound's maximal response divided by the isoproterenol maximal response times 100.

In vitro Rat Atrial Tachycardia

Male rats (250–350 g) (Harlan Sprague Dawley, Indianapolis, Ind., USA) are killed by cervical dislocation. Hearts are removed and the left and right atria are dissected and mounted with thread in tissue baths containing 10 mls of modified Krebs' solution. Initial resting tension is 1.5–2.0 g at the outset of the experiment (*Naunyn-Schmied Arch. Pharmacol.*, 320:145, 1982). Tissues are allowed to equilibrate approximately 30 minutes with vigorous oxygenation before exposure to a compound of the invention.

To evaluate the ability of test compounds to increase heart rate, representative compounds of the present invention are added cumulatively once the atrial rate reached a steady state from the previous addition. Compound addition is continued until no further increase in atrial rate occurred or until a concentration of $10^{-4}$M is reached. The increase in beats per minute (bpm) is measured for each concentration of test compound by means of a BioPac System (*Br. J of Pharmacol.*, 126:1018–1024, 1999).

Relative to a compound of formula I where $R^1$, $R^{1a}$, $R^2$, $R^3$ and $R^4$ are hydrogen, $R^5$ and $R^6$ are both methyl, $X^2$ is O, and $R^7$ is 5-carboxamido-pyrid-2-yl (not claimed, generically disclosed in U.S. Pat. No. 5,786,356), corresponding compounds of the present invention exhibit a reduction in atrial tachycardia.

Utilities

As agonists of the $\beta_3$ receptor, the salts of the present invention are useful in treating conditions in human and non-human animals in which the $\beta_3$ receptor has been demonstrated to play a role.

The diseases, disorders or conditions for which compounds of the present invention are useful in treating include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) hypertension, (9) disorders of the gall bladder including acute and chronic cholecystitis, (10) depression, (11) elevated intra-ocular pressure and glaucoma, (12) non-specific diarrhea dumping syndrome, (13) hepatic steatosis [fatty degeneration of the liver], and obesity dependent diseases/disorders such as: (14) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (15) irritable bowel syndrome and other disorders needing decreased gut motility, (16) diabetic retinopathy, (17) neuropathic bladder dysfunction, (18) osteoarthritis, (19) restrictive lung disease, (20) obstructive sleep apnea, (21) congestive heart failure, (22) venous stasis and skin disorders related to venous stasis, (23) decreased libido (in both males and females), and (24) acute and chronic cystitis. The term "obesity dependent" means that the symptoms of said diseases will be ameliorated via the present salt's effect on the patient's weight.

Human patients in need of obesity treatment are typically those with a body mass index (BMI)>27 or those with a BMI≧5 when co-morbidities, e.g., hypertension, sleep apnea and/or osteoarthritis, are present. A patient population at particular need of treatment are those with a BMI≧30 or ≧27 with co-morbidities.

Human patients in need of hypertension treatment are frequently overweight individuals, i.e., those with a BMI≧5, but may also be of normal body weight (i.e., BMI<25).

Human patients in need of type 2 diabetes treatment are typically individuals with a BMI<25, i.e., individuals that are not overweight.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Formulation Examples

| Formulation 1 Tablets | |
| --- | --- |
| Ingredient | Quantity (mg/tablet) |
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

| Formulation 2 Suspensions | |
| --- | --- |
| Ingredient | Quantity (mg/5 ml) |
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

| Formulation 3 Intravenous Solution | |
|---|---|
| Ingredient | Quantity |
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include; the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances.

Generally, an effective minimum daily dose of a compound of formula I is about 5, 10, 15, or 20 mg. Typically, an effective maximum dose is about 500, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds can be administered by a variety of routes including the oral, rectal, transdermal, subcutaneous, topical, intravenous, intramuscular or intranasal routes.

Combination Therapy

The compound of formula I may be used in combination with other drugs that are used in the treatment of the diseases or conditions for which the present salts are useful, e.g., treatment of obesity and/or type 2 diabetes. Such other drug(s) may be administered, by a route and in an amount commonly used therefore, contemporaneously or sequentially with a compound of the present invention. When a compound of the present invention is used contemporaneously with one or more other drugs, a pharmaceutical unit dosage form containing such other drugs in addition to the present salt is preferred. Accordingly, the pharmaceutical compositions of the present invention include those that also contain one or more other active ingredients, in addition to a compound of the present invention.

We claim:

1. A compound of formula I:

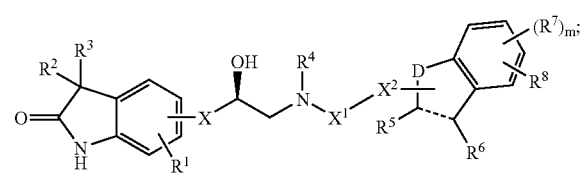

wherein the dashed line represents a single or double bond;

m is 0, 1 or 2;

D is O or S;

$R^1$ is H, CN, halo, $C_1$–$C_6$ alkyl, $C_1$–$C_4$ haloalkyl, $CO_2R^{10}$, $CONR^{10}R^{10}$, $NR^{10}COR^{10}$, $NR^{10}R^{10}$, $OR^{10}$, $SR^{10}$, $SOR^{10}$, $SO_2R^{10}$ or $SO_2NR^{10}R^{10}$;

$R^2$ is H, $C_1$–$C_6$ alkyl or benzyl;

$R^3$ is $C_1$–$C_6$ alkyl or benzyl;

or $R^2$ and $R^3$ combine with the carbon to which each are attached to form a $C_3$–$C_7$ carbocyclic ring; provided that if $R^3$ is $C_2$–$C_6$ alkyl or benzyl, then $R^2$ must be hydrogen;

$R^4$ is H or $C_1$–$C_6$ alkyl;

$R^5$ forms a bond with $X^2$ or is H, cyano, $C_1$–$C_6$ alkyl, $CONR^{11}R^{11}$ or $CO_2R^{11}$;

$R^6$ forms a bond with $X^2$ or is H or $C_1$–$C_6$ alkyl;

$R^7$ is independently at each occurrence halo, hydroxy, cyano, $C_1$–$C_6$ alkyl, $C_1$–$C_4$ haloalkyl or $C_1$–$C_6$ alkoxy;

$R^8$ is H, $CO_2R^{12}$, $CONR^{12}R^{12}$, $CH=CHR^{13}$, $CH_2CH_2R^{13}$, $NR^{12}R^{12}$, $NR^{12}SO_2R^{12}$, $O(CR^{14}R^{15})_nR^{16}$, $O(CR^{14}R^{15})_pR^{17}$, $SO_2R^{12}$, $SO_2NR^{12}R^{12}$, optionally substituted phenyl or optionally substituted heterocycle;

$R^9$ forms a bond with $X^2$ or is H or $C_1$–$C_6$ alkyl;

$R^{10}$, $R^{11}$ and $R^{12}$ are independently at each occurrence H, $C_1$–$C_6$ alkyl or phenyl; or when two $R^{10}$ or two $R^{11}$ or two $R^{12}$ moieties are connected to the same nitrogen atom, then said $R^{10}$ or $R^{11}$ or $R^{12}$ moieties may combine with the nitrogen to which they are attached to form a pyrollidinyl, piperidinyl or hexamethyleneimino ring;

$R^{13}$ is cyano, $CO_2R^{18}$, $CONR^{18}R^{18}$, $CONR^{18}SO_2R^{18}$, $SO_2R^{18}$, heterocycle or optionally substituted phenyl;

$R^{14}$ and $R^{15}$ are independently at each occurrence H or $C_1$–$C_6$ alkyl;

$R^{16}$ is hydrogen, $CO_2R^{19}$, $CONR^{19}R^{19}$, $SO_2R^{19}$, $SO_2NR^{19}R^{19}$, optionally substituted phenyl or optionally substituted heterocycle, $R^{17}$ is cyano, $NR^{20}R^{20}$, $NR^{20}SO_2R^{20}$ or $OR^{20}$;

$R^{18}$, $R^{19}$ and $R^{20}$ are independently at each occurrence H, $C_1$–$C_6$ alkyl or phenyl; or when two $R^{18}$ or two $R^{19}$ or two $R^{20}$ moieties are connected to the same nitrogen atom, then said $R^{18}$ or $R^{19}$ or $R^{20}$ moieties may combine with the nitrogen to which they are attached to form a pyrollidinyl, piperidinyl or hexamethyleneimino ring;

n is 0, 1, 2 or 3;

p is 1, 2 or 3;

X is $OCH_2$, $SCH_2$ or a bond;

$X^1$ is a bond or $(CR^{21}R^{22})_q$;

$X^2$ is a bond, CO, $CONR^{23}$ or $NR^{23}CO$; q is 1, 2, 3, 4 or 5;

$R^{21}$ and $R^{22}$ are independently at each occurrence H or $C_1$–$C_6$ alkyl; or $R^{21}$ and $R^{22}$ combine with the carbon to which they are both attached to form a carbocyclic $C_3$–$C_7$ ring; and $R^{23}$ is H or $C_1$–$C_6$ alkyl; or a pharmaceutical salt thereof.

2. The compound of claim 1 which is the hydrochloride salt.

3. A method of treating Type 2 Diabetes comprising administering to a patient in need thereof a compound of claim 1.

4. A method of treating obesity comprising administering to a patient in need thereof a compound of claim 1.

* * * * *